(12) United States Patent
Fuchss et al.

(10) Patent No.: US 7,790,710 B2
(45) Date of Patent: Sep. 7, 2010

(54) IMIDAZOPYRIDINE DERIVATIVES USEFUL AS INOS INHIBITORS

(75) Inventors: Thomas Fuchss, Radolfzell (DE);
Andreas Strub, Radolfzell (DE);
Wolf-Rüdiger Ulrich, Constance (DE);
Christian Hesslinger, Zoznegg (DE);
Martin Lehner, Constance (DE);
Raimund Külzer, Radolfzell (DE);
Rainer Boer, Constance (DE); Manfrid Eltze, Constance (DE)

(73) Assignee: NYCOMED GmbH, Constance (DE)

( * ) Notice: Subject to any disclaimer, the term of this patent is extended or adjusted under 35 U.S.C. 154(b) by 250 days.

(21) Appl. No.: 11/886,785

(22) PCT Filed: Mar. 29, 2006

(86) PCT No.: PCT/EP2006/061141
§ 371 (c)(1),
(2), (4) Date: Oct. 11, 2007

(87) PCT Pub. No.: WO2006/103255
PCT Pub. Date: Oct. 5, 2006

(65) Prior Publication Data
US 2009/0131399 A1    May 21, 2009

(30) Foreign Application Priority Data
Mar. 31, 2005    (EP) .................... 05102558

(51) Int. Cl.
*A01N 43/00* (2006.01)
*A61K 31/55* (2006.01)
*A01N 43/46* (2006.01)
*A01N 43/90* (2006.01)
*A61K 31/519* (2006.01)
*C07D 413/00* (2006.01)
*C07D 415/00* (2006.01)
*C07D 417/00* (2006.01)
*C07D 419/00* (2006.01)
*C07D 513/02* (2006.01)
*C07D 515/02* (2006.01)
*C07D 403/02* (2006.01)

(52) U.S. Cl. .................... 514/215; 514/264.1; 540/599; 546/118; 548/302.4; 548/314.7

(58) Field of Classification Search ................ 514/215, 514/264.1; 540/599; 546/118; 548/302.4, 548/314.7
See application file for complete search history.

(56) References Cited

FOREIGN PATENT DOCUMENTS

| EP | 0 505 321 A2 | 9/1992 |
|---|---|---|
| WO | 96/33175 A1 | 10/1996 |
| WO | 02/10139 A1 | 2/2002 |
| WO | 03/080607 A1 | 10/2003 |
| WO | 2004/076451 A1 | 9/2004 |
| WO | 2005/061496 A1 | 7/2005 |

OTHER PUBLICATIONS

Tinker AC and Wallace AV, "Selective Inhibitors of Inducible Nitric Oxide Synthase: Potential Agents for the Treatment of Inflammatory Diseases?" Current Topics in Medicinal Chemistry, 2006, 6(2), 77-92 (abstract provided).*
Benati, L., et al., "Reactions of Benzocyclic β-Keto Esters with Sulfonyl azides. 2. Further Insight into the Influence of Azide Structure and Solvent on the Reaction Course", J. Org. Chem., vol. 64, pp. 5132-5138, (1999).
Connop, B. P., et al., "Attenuation of Malonate-induced Degeneration of the Nigrostriatal Pathway by Inhibitors of Nitric Oxide Synthase",Neuropharmacology, vol. 35, No. 4, pp. 459-465, (1996).
Cai, S. X., et al., "5-(N-Oxyaza)-7-substituted-1,4-dihydroquinoxaline-2,3-diones: Novel, Systemically Active and Broad Spectrum Antagonists for NMDA/glycine, AMPA, and Kainate Receptors",J. Med. Chem., vol. 40, pp. 3679-3686, (1997).
Corbett, J. A., et al., "Nitric oxide production in islets from nonobese diabetic mice: Aminoguanidine-sensitive and -resistant stages in the immunological diabetic process", Proc. Natl. Acad. Sci. USA, vol. 90, pp. 8992-8995, (1993).
Connor, J. R., "Suppression of adjuvant-induced arthritis by selective inhibition of inducible nitric oxide synthase", European Journal of Pharmacology, vol. 273, pp. 15-24, (1995).
Benati, L., et al., "Radical Chain Reactions of α-Azido-β-keto Esters with Tributyltin Hydride. A Novel Entry to Amides and Lactams through Regiospecific Nitrogen Insertion", J. Org. Chem, vol. 64, pp. 7836-7841, (1999).
Bagasra, O., et al., "Absence of the inducible form of nitric oxide synthase in the brains of patients with the acquired immunodeficiency syndrome", Journal of Neuro Virology, vol. 3, pp. 153-167, (1997).
De Belder, A. J., et al., "Myocardial calcium-independent nitric oxide synthase activity is present in dilated cardiomyopathy, myocarditis, and postpartum cardiomyopathy but not in ischaemic or valvar heart disease", Br Heart J, vol. 74, pp. 426-430, (1995).

(Continued)

*Primary Examiner*—San-ming Hui
*Assistant Examiner*—Paul Zarek
(74) *Attorney, Agent, or Firm*—The Nath Law Group; Joshua B. Goldberg; Sheldon M. McGee

(57) ABSTRACT

The compounds of formula (I)

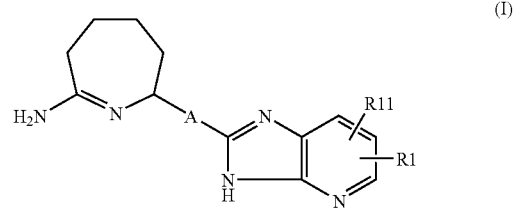

in which R1, R11 and A have the meanings as given in the description are novel effective iNOS inhibitors.

10 Claims, No Drawings

OTHER PUBLICATIONS

De Angelo, Nitric oxide scavengers in the treatment of shock associated with systemic inflammatory response syndrome, J., Exp. Opin. Pharmacother., vol. 1, No. 1, pp. 19-29, (1999).

Pelletier, J-P., et al., "Reduced Progression of Experimental Osteoarthritis in Vivo by Selective Inhibition of Inducible Nitric Oxide Synthase", Arthritis & Rheumatism, vol. 41, No. 7, pp. 1275-1286, (1998).

Parkinson, J. F., et al., "The role of nitric oxide in multiple sclerosis", J Mol Med, vol. 75, pp. 174-186, (1997).

Narita, I., et al., "Nitric Oxide Mediates Immunologic Injury to Kidney Mesangium in Experimental Glomerulonephritis", Laboratory Investigation, vol. 72, No. 1, p. 17, (1995).

Mesenge, C., et al., "Reduction of the Neurological Deficit in Mice with Traumatic Brain Injury by Nitric Oxide Synthase Inhibitors", Journal of Neurotrauma, vol. 13, No. 4, pp. 209-214, (1996).

Kristof, A. S., et al., "Role of Inducible Nitric Oxide Synthase in Endotoxin-induced Acute Lung Injury", Am J Respir Crit Care Med, vol. 158, pp. 188-1889, (1998).

Korytko, P. J., et al., "Pharmacological Characterization of Nitric Oxide Production in a Rat Model of Meningitis", Neuropharmacology, vol. 35, No. 2, pp. 231-237, (1996).

Ishii, K., et al., "Subacute NO generation induced by Alzheimer's β-amyloid in the living brain: reversal by inhibition of the inducible NO synthase", Faseb J., vol. 14, pp. 1485-1489, (2000).

Redl, H., et al., "Treatment with the NO-synthase inhibitor 546C88 Twelve Hours After Start of *E. coli* Bacteremia is Beneficial in a Baboon Model of Septic Shock", Shock, Abstracts, Suppl. 51, No. 145, (1997).

Wada, K., et al., "Inducible Nitric Oxide Synthase Expression after Traumatic Brain Injury and Neuroprotection with Aminoguanidine Treatment in Rats", Neurosurgery, vol. 43, pp. 1427-1436, (1998).

Wang, D., et al., "Reduction of Myocardial Infarct Size by Inhibition of Inducible Nitric Oxide Synthase", AJH, vol. 12, pp. 174-182, (1999).

Tozer, G. M., et al., "Nitric Oxide in Tumour Biology and Cancer Therapy. Part 2.: Therapeutic Implications", Clinical Oncology, vol. 9, pp. 357-364, (1997).

Strand, O. A., et al., "NG-monomethyl-L-arginine improves survival in a pig model of abdominal sepsis", Crit Care Med, vol. 26, No. 9, pp. 1490-1499, (1998).

Sun, X., et al., "Cardiodepressant Effects of Interferon-γ and Endotoxin Reversed by Inhibition of NO Synthase 2 in Rat Myocardium", J Mol Cell Cardiol, vol. 30, pp. 989-997, (1998).

Zingarelli, B., et al., "Reduced oxidative and nitrosative damage in murine experimental colitis in the absence of inducible nitric oxide synthase", Gut, vol. 45, pp. 199-209, (1999).

Iadecola, C., et al., "Inducible Nitric Oxide Synthase Gene Expression in Vascular Cells After Transient Focal Cerebral Ischemia", Stroke A Journal of Cerebral Circulation, vol. 27, No. 8, pp. 1373-1380, (1996).

\* cited by examiner

IMIDAZOPYRIDINE DERIVATIVES USEFUL AS INOS INHIBITORS

This application was filed under 35 U.S.C. 371 as a national stage of PCT/EP2006/061141, filed Mar. 29, 2006.

FIELD OF APPLICATION OF THE INVENTION

The invention relates to novel imidazopyridine derivatives, which are used in the pharmaceutical industry for the production of pharmaceutical compositions.

KNOWN TECHNICAL BACKGROUND

The International Application WO 03/80607 describes alkoxypyridine derivatives with inducible nitric oxide synthase (iNOS) inhibitory activity. The International Application WO 96/33175 contains cyclic amidino agents useful as nitric oxide synthase (NOS) inhibitors. WO 2004/076451 relates to imidazo[4,5-b]quinoline derivatives and their use as NOS inhibitors. WO 02/10139 describes hexahydro-7-1H-azepin-2-yl-hexanoic acid derivatives as iNOS inhibitors.

DESCRIPTION OF THE INVENTION

It has now been found that the novel 7-amino-3,4,5,6-tetrahydro-2H-azepin-2-yl-substituted imidazopyridine derivatives, which are described in greater details below, have surprising and particularly advantageous properties.

The invention thus relates to compounds of formula I

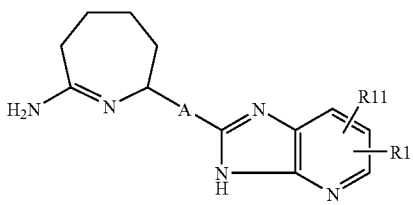

(I)

in which
A is 1-4C-alkylene or 3-7C-cycloalkylene,
R1 is phenyl, R2- and/or R3-substituted phenyl, Har1, or R4- and/or R5-substituted Har1,
R11 is hydrogen, halogen, 1-4C-alkyl or 1-4C-alkoxy, in which
R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22, in which
R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which
Har2 is pyridyl, thienyl, furyl or tetrahydrofuryl,
R211 is 1-4C-alkyl, halogen, 1-4C-alkoxy, or mono- or di-1-4C-alkylamino,
R212 is 1-4C-alkyl or halogen,
R22 is hydrogen, 1-4C-alkyl, hydroxy-2-4C-alkyl or 1-4C-alkoxy-2-4C-alkyl, or R21 and R22 together and with inclusion of the nitrogen atom, to which they are bonded, form a heterocyclic ring Het1, in which
Het1 is a fully saturated or partially unsaturated mono- or fused bicyclic ring or ring system made up of
a first constituent being a 3- to 7-membered monocyclic fully saturated non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzene ring,
and which ring Het1 is optionally substituted by R23 on a ring carbon atom,
and/or which ring Het1 is optionally substituted by R24 on a further ring carbon atom,
and/or which ring Het1 is optionally substituted by an ethylenedioxy group on a ring carbon atom,
and/or which ring Het1 is optionally substituted by R25 on a ring nitrogen atom, in which
R23 is 1-4C-alkyl, 1-4C-alkoxy or phenylcarbonyl,
R24 is 1-4C-alkyl or 1-4C-alkoxy,
R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which
R251 is halogen, cyano or 1-4C-alkyl,
R252 is halogen or 1-4C-alkyl,
R3 is hydrogen, 1-4C-alkyl, halogen, trifluoromethyl, 1-4C-alkoxy, or completely or predominantly fluorine-substituted 1-4C-alkoxy,
Har1 is bonded to the parent molecular group via a ring carbon atom, and is a monocyclic or fused bicyclic 5- to 10-membered unsaturated or partially saturated heteroaryl radical comprising one to three heteroatoms, each of which is selected from a group consisting of nitrogen, oxygen and sulfur,
R4 is 1-4C-alkyl, halogen, cyano, trifluoromethyl, phenyl, mono- or di-1-4C-alkylamino, formyl, 1-4C-alkylcarbonyl, carboxyl or 1-4C-alkoxy,
R5 is 1-4C-alkyl or halogen, the enantiomers, as well as the salts of these compounds and enantiomers.

Preferably, the invention relates to compounds of formula I in which
A is 1-4C-alkylene or 3-7C-cycloalkylene,
R1 is phenyl, R2- and/or R3-substituted phenyl, Har1, or R4- and/or R5-substituted Har1,
R11 is hydrogen, halogen, 1-4C-alkyl or 1-4C-alkoxy, in which
R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22, in which
R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which Har2 is pyridyl, thienyl or furyl, R211 is 1-4C-alkyl, halogen, 1-4C-alkoxy, or mono- or di-1-4C-alkylamino, R212 is 1-4C-alkyl or halogen, R22 is hydrogen, 1-4C-alkyl, hydroxy-2-4C-alkyl or 1-4C-alkoxy-2-4C-alkyl, or R21 and R22 together and with inclusion of the nitrogen atom, to which they are bonded, form a heterocyclic ring Het1, in which Het1 is a fully saturated or partially unsaturated mono- or fused bicyclic ring or ring system made up of
  a first constituent being a 3- to 7-membered monocyclic fully saturated non-aromatic heterocyclic ring B,
    which heterocyclic ring B comprises one to three heteroatoms independently selected from nitrogen, oxygen and sulfur,
    and which heterocyclic ring B is optionally substituted by one or two oxo groups,
  and, optionally, fused to said first constituent,
  a second constituent being a benzene ring,
  and which ring Het1 is optionally substituted by R23 on a ring carbon atom,
  and/or which ring Het1 is optionally substituted by R24 on a further ring carbon atom,
  and/or which ring Het1 is optionally substituted by an ethylenedioxy group on a ring carbon atom,
  and/or which ring Het1 is optionally substituted by R25 on a ring nitrogen atom, in which R23 is 1-4C-alkyl, 1-4C-alkoxy or phenylcarbonyl, R24 is 1-4C-alkyl or 1-4C-alkoxy, R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, Har1 is bonded to the parent molecular group via a ring carbon atom, and is a monocyclic or fused bicyclic 5- to 10-membered unsaturated or partially saturated heteroaryl radical comprising one to three heteroatoms, each of which is selected from a group consisting of nitrogen, oxygen and sulfur, R4 is 1-4C-alkyl, halogen, cyano, trifluoromethyl, phenyl, mono- or di-1-4C-alkylamino, formyl, 1-4C-alkylcarbonyl, carboxyl or 1-4C-alkoxy, R5 is 1-4C-alkyl or halogen, the enantiomers, as well as the salts of these compounds and enantiomers.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

2-4C-Alkyl is a straight-chain or branched alkyl radical having 2 to 4 carbon atoms. Examples are the butyl, isobutyl, sec-butyl, tert-butyl, propyl, isopropyl and, particularly, ethyl radical.

1-4C-Alkylene is a straight chain alkylene radical having 1 to 4 carbon atoms. Examples which may be mentioned in this context are the methylene (—$CH_2$—), ethylene (—$CH_2$—$CH_2$—), trimethylene (—$CH_2$—$CH_2$—$CH_2$—) and the tetramethylene (—$CH_2$—$CH_2$—$CH_2$—$CH_2$—) radical.

3-7C-Cycloalkylene represents cycloalkylene radicals having 3 to 7 carbon atoms. The 1,2-cyclopropylene radical is thereof preferred.

1-4C-Alkoxy is a radical which, in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, and, particularly, the ethoxy and methoxy radicals.

3-7C-Cycloalkyl stands for cyclopropyl, cyclobutyl, cyclopentyl, cyclohexyl and cycloheptyl, of which cyclopropyl, cyclobutyl and cyclopentyl are preferred.

3-7C-Cycloalkylmethyl stands for a methyl radical, which is substituted by one of the abovementioned 3-7C-cycloalkyl radicals. Examples which may be mentioned are the cyclopropylmethyl and the cyclohexylmethyl radicals.

Halogen within the meaning of the present invention is iodine, bromine, or, particularly, chlorine or fluorine.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

1-4C-Alkoxy-2-4C-alkyl stands for one of the abovementioned 2-4C-alkyl radicals which is substituted by one of the abovementioned 1-4C-alkoxy radicals. Examples which may be mentioned are the 2-(methoxy)ethyl (—$CH_2$—$CH_2$—O—$CH_3$), the 3-(methoxy)propyl (—$CH_2$—$CH_2$—$CH_2$—O—$CH_3$), the 2-(ethoxy)ethyl (—$CH_2$—$CH_2$—O—$CH_2$—$CH_3$) and the 2-(isopropoxy)ethyl (—$CH_2$—$CH_2$—O—CH—($CH_3$)$_2$) radical.

Hydroxy-2-4C-alkyl stands for one of the abovementioned 2-4C-alkyl radicals which is substituted by a hydroxyl radical. Examples which may be mentioned are the 2-hydroxyethyl and the 3-hydroxypropyl radical.

Mono- or di-1-4C-alkylamino radicals contain in addition to the nitrogen atom, one or two of the abovementioned 1-4C-alkyl radicals. Particularly worthy to be mentioned are the di-1-4C-alkylamino radicals, especially the dimethylamino, the diethylamino and the diisopropylamino radical.

Mono- or di-1-4C-alkylaminocarbonyl radicals contain in addition to the carbonyl group one of the abovementioned mono- or di-1-4C-alkylamino radicals. Examples which may be mentioned are the N-methyl-, the N,N-dimethyl-, the N-ethyl-, the N-propyl-, the N,N-diethyl- and the N-isopropylaminocarbonyl radical.

An 1-4C-alkylcarbonylamino radical is, for example, the propionylamino [$C_3H_7$C(O)NH—] and the acetylamino radical [$CH_3$C(O)NH—].

1-4C-Alkoxycarbonyl is a carbonyl group to which one of the abovementioned 1-4C-alkoxy radicals is bonded. Examples are the methoxycarbonyl [$CH_3$O—C(O)—] and the ethoxycarbonyl [$CH_3CH_2$O—C(O)—] radical.

Phenyl-1-4C-alkoxy stands for one of the abovementioned 1-4C-alkoxy radicals, which is substituted by the phenyl radical. Examples which may be mentioned are the benzyloxy and the phenethoxy radical.

Mono- or di-1-4C-alkylamino-2-4C-alkyl stands for one of the abovementioned 2-4C-alkyl radicals which is substituted by one of the abovementioned mono- or di-1-4C-alkylamino radicals. An example which may be mentioned is the 2-(dimethylamino)ethyl radical.

Phenyl-1-4C-alkyl stands for one of the abovementioned 1-4C-alkyl radicals, which is substituted by a phenyl radical. Examples which may be mentioned are the phenethyl and the benzyl radical.

Har2-1-4C-alkyl stands for one of the abovementioned 1-4C-alkyl radicals, which is substituted by an Har2 radical. Examples which may be mentioned are the 2-(Har2)-ethyl and the (Har2)-methyl radicals.

Har2 stands for pyridyl, thienyl, furyl or tetrahydrofuryl.

1-4C-Alkylcarbonyl is a carbonyl group to which one of the abovementioned 1-4C-alkyl radicals is bonded. An example is the acetyl [$CH_3$—C(O)—] radical.

1-4C-Alkylsulfonyl is a sulfonyl group to which one of the abovementioned 1-4C-alkyl radicals is bonded. An example is the methanesulfonyl ($CH_3SO_2$—) or ethanesulfonyl ($CH_3CH_2SO_2$—) radical.

Het1 refers to a fully saturated or partially unsaturated mono- or fused bicyclic ring or ring system made up of
a first constituent being a 3- to 7-membered monocyclic fully saturated non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzene ring,
and which ring Het1 is optionally substituted by R23 on a ring carbon atom,
and/or which ring Het1 is optionally substituted by R24 on a further ring carbon atom,
and/or which ring Het1 is optionally substituted by an ethylenedioxy group on a ring carbon atom,
and/or which ring Het1 is optionally substituted by R25 on a ring nitrogen atom.

Examples for Het1 may include, but are not limited to, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl, and the oxo substituted derivatives of the aforementioned examples such as e.g. 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl or 5-oxo-1,4-diazepanyl, as well as thiomorpholine S-oxide or thiomorpholine S,S-dioxide, and the benzo-fused derivatives of the aforementioned examples such as e.g. indolinyl, isoindolinyl, 1,2,3,4-tetrahydroquinolinyl or 1,2,3,4-tetrahydroisoquinolinyl.

As used herein, the term "oxo" forms a carbonyl moiety when attached at a carbon atom, a sulfoxide moiety when attached to a sulfur atom and a sulfonyl moiety when two of said terms are attached to a sulfur atom.

In one detail, Het1 is piperidinyl, pyrrolidinyl or azetidinyl, or morpholinyl, thiomorpholinyl, S-oxo-thiomorpholinyl or S,S-dioxo-thiomorpholinyl.

In another detail, Het1 is indolinyl, isoindolinyl, 1,2,3,4-tetrahydroquinolinyl or 1,2,3,4-tetrahydroisoquinolinyl.

In another detail, Het1 is substituted by R23 and/or R24 on the benzene moiety, and is indolinyl, isoindolinyl, 1,2,3,4-tetrahydroquinolinyl or 1,2,3,4-tetrahydroisoquinolinyl.

In another detail, Het1 is piperazinyl or homopiperazinyl.

In another detail, Het1 is 4N—(R25)-piperazinyl or 4N—(R25)-homopiperazinyl.

In another detail, Het1 is 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl or 5-oxo-1,4-diazepanyl.

In another detail, Het1 is 3-(R25)-imidazolidin-2-one-yl, 3-(R25)-imidazolidin-2,5-dione-yl, 4-(R25)-piperazine-2-one-yl, 4-(R25)-piperazine-2,6-dione-yl or 4-(R25)-1,4-diazepan-5-one-yl.

In another detail, Het1 is substituted by R23 or by ethylenedioxy on one ring carbon atom, and is piperidinyl.

In another detail, Het1 is azetidin-1-yl or 4N—(R25)-piperazin-1-yl.

Har1 refers to a monocyclic or fused bicyclic 5- to 10-membered unsaturated or partially saturated heteroaryl radical comprising one to three heteroatoms, each of which is selected from a group consisting of nitrogen, oxygen and sulfur. Particularly, Har1 refers to a monocyclic or fused bicyclic 5- to 10-membered unsaturated heteroaryl (heteroaromatic) radical comprising one to three heteroatoms, each of which is selected from a group consisting of nitrogen, oxygen and sulfur. More particularly, Har1 refers to a monocyclic 5- to 6-membered or fused bicyclic 9- to 10-membered unsaturated heteroaryl (heteroaromatic) radical comprising one to three heteroatoms, each of which is selected from a group consisting of nitrogen, oxygen and sulfur.

Exemplary Har1 radicals may include, without being restricted to, the 5-membered derivatives furanyl, thienyl, pyrrolyl, oxazolyl, isoxazolyl, thiazolyl, isothiazolyl, imidazolyl, pyrazolyl, triazolyl (precisely: 1,2,4-triazolyl or 1,2,3-triazolyl), thiadiazolyl (precisely: 1,3,4-thiadiazolyl, 1,2,5-thiadiazolyl, 1,2,3-thiadiazolyl or 1,2,4-thiadiazolyl) or oxadiazolyl (precisely: 1,3,4-oxadiazolyl, 1,2,5-oxadiazolyl, 1,2,3-oxadiazolyl or 1,2,4-oxadiazolyl), or the 6-membered derivatives pyridinyl, pyrimidinyl, pyrazinyl or pyridazinyl; or the benzo-fused derivatives thereof, such as e.g. the 9-membered derivatives benzothienyl, benzofuranyl, indolyl, benzoxazolyl, benzothiazolyl, indazolyl, benzimidazolyl, benzisoxazolyl, benzisothiazolyl, benzofurazanyl, benzotriazolyl, benzothiadiazolyl, isoindolyl, isofuranyl or isobenzothienyl, or the 10-membered derivatives quinolinyl, isoquinolinyl, quinazolinyl, quinoxalinyl, phthalazinyl or cinnolinyl; or indolizinyl or naphthyridinyl.

It is to be noted, that the Har1 radical is bonded to the pyridine ring of the imidazopyridine scaffold via a ring carbon atom.

In one detail, as exemplary unsubstituted or R4- and/or R5-substituted Har1 radicals may be mentioned, for example, without being restricted thereto, thien-2-yl, thien-3-yl, furan-2-yl, furan-3-yl, 3-methyl-thien-2-yl, 4-methyl-thien-2-yl, 5-methyl-thien-2-yl, 5-ethyl-thien-2-yl, 4-methyl-furan-2-yl, 5-methyl-furan-2-yl, 5-phenyl-thien-2-yl, benzofuran-2-yl, benzothien-2-yl, benzothien-3-yl, benzoxazol-5-yl, benzthiazol-5-yl, 1-methyl-indol-5-yl, 1H-indol-2-yl, 1H-indol-3-yl, 1H-indol-4-yl, 1H-indol-5-yl, 1H-indol-6-yl, 6-trifluoromethyl-indol-2-yl, 7-trifluoromethyl-indol-2-yl, 5-methoxy-indol-2-yl, 1H-pyrrol-2-yl, pyrrazol-4-yl, imidazol-4-yl, pyridin-2-yl, pyridin-3-yl, pyridin-4-yl, 4-methyl-pyridin-2-yl, 5-methyl-pyridin-2-yl, 6-methyl-pyridin-2-yl, 5-methyl-pyridin-3-yl, 2-methyl-pyridin-4-yl, 3-methyl-pyridin-4-yl, 6-methoxy-pyridin-2-yl, 2-methoxy-pyridin-3-yl, 4-methoxy-pyridin-3-yl, 5-methoxy-pyridin-3-yl, 6-methoxy-pyridin-3-yl, pyrimidin-5-yl, 2-methoxy-pyrimidin-5-yl, quinolin-3-yl, quinolin-4-yl, quinolin-5-yl, quinolin-6-yl, quinolin-8-yl, isoquinolin-4-yl, isoquinolin-5-yl, 5-cyano-thien-2-yl, 5-carboxy-thien-2-yl, 3-carboxy-thien-2-yl, 5-dimethylamino-thien-2-yl, 2-acetyl-thien-3-yl, 5-acetyl-thien-2-yl, 3,5-dimethylisoxazol-4-yl, 4-chloro-thien-2-yl, 5-chloro-thien-2-yl, 3-fluoro-pyridin-4-yl, 3-chloro-pyridin-4-yl, 6-fluoro-pyridin-3-yl, 6-chloro-pyridin-3-yl, 2-fluoropyridin-3-yl, 2-chloro-pyridin-3-yl, 2-chloro-3-fluoro-pyridin-4-yl, 2-chloro-5-fluoro-pyridin-3-yl, 2,3-dichloro-pyridin-4-yl, 3,5-difluoro-pyridin-4-yl, 2,6-dichloro-pyridin-3-yl, 2-fluoro-6-methyl-pyridin-3-yl, 6-fluoro-2-methyl-pyridin-3-yl, 6-fluoro-5-methyl-pyridin-3-yl, 6-chloro-5-methyl-pyridin-3-yl, 2-chloro-6-methyl-pyridin-3-yl, 5,6-difluoro-indol-2-yl, or 5-chloro-indol-2-yl, as well as benzimidazol-2-yl or 5-methyl-benzimidazol-2-yl.

In general, unless otherwise mentioned, the heterocyclic groups mentioned herein refer to all of the possible isomeric forms thereof.

The heterocyclic groups mentioned herein refer, unless otherwise noted, in particular to all of the possible positional isomers thereof.

Thus, for example, the term pyridyl or pyridinyl includes pyridin-2-yl, pyridin-3-yl and pyridin-4-yl.

Constituents which are optionally substituted as stated herein, may be substituted, unless otherwise noted, at any possible position.

The carbocyclic groups, alone or as part of other groups, mentioned herein may be substituted by their given substituents, unless otherwise noted, at any substitutable ring carbon atom.

The heterocyclic groups, alone or as part of other groups, mentioned herein may be substituted by their given substituents, unless otherwise noted, at any possible position, such as e.g. at any substitutable ring carbon or ring nitrogen atom.

Unless otherwise noted, rings containing quaternizable imino-type ring nitrogen atoms (—N=) may be preferably not quaternized on these imino-type ring nitrogen atoms by the mentioned substituents.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminum, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to experts knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

A person skilled in the art knows on the base of his/her expert knowledge that the compounds according to this invention can exist, with regard to the fused imidazo ring, in different tautomeric forms such as e.g. in the 1-H form or, preferably, in the 3-H form, which is shown in formula I. The invention includes all conceivable tautomers in pure form as well as in any mixing ratio. Particularly the present invention includes the pure 1-H- and, preferably, 3-H-tautomers as well as any mixtures thereof.

Additionally, a person skilled in the art knows on the base of his/her expert knowledge that the compounds according to this invention can exist, with regard to the cyclic amidine structure in the amino-azepine ring, also in different tautomeric forms such as e.g. in the exocyclic imine form or, preferably, in the exocyclic amine form, which is shown in formula I. The invention includes all conceivable tautomers in pure form as well as in any mixing ratio. Particularly the present invention includes the pure exocyclic imine- and, preferably, amine-tautomers as well as any mixtures thereof.

Preferred compounds according to the present invention are those compounds of formula I in which A is ethylene or cyclopropylene, R1 is bonded to the 6-position of the imidazopyridine scaffold, and is phenyl, R2- and/or R3-substituted phenyl, or Har1, R11 is hydrogen, in which R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22, in which R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which Har2 is pyridyl, thienyl, furyl or tetrahydrofuryl, R211 is 1-4C-alkyl, halogen, 1-4C-alkoxy, or mono- or di-1-4C-alkylamino, R212 is 1-4C-alkyl or halogen, R22 is hydrogen, hydroxy-2-4C-alkyl, 1-4C-alkoxy-2-4C-alkyl or 1-4C-alkyl, or R21 and R22 together and with inclusion of the nitrogen atom, to which they are bonded, form a heterocyclic ring Het1, in which Het1 is piperidinyl, pyrrolidinyl, azetidinyl, morpholinyl, thiomorpholinyl, S-oxo-thiomorpholinyl or S,S-dioxo-thiomorpholinyl, or indolinyl, isoindolinyl, 1,2,3,4-tetrahydroquinolinyl or 1,2,3,4-tetrahydroisoquinolinyl, or piperazinyl or homopiperazinyl, or 4N—(R25)-piperazinyl or 4N—(R25)-homopiperazinyl, 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl or 5-oxo-1,4-diazepanyl, 3-(R25)-imidazolidin-2-one-yl, 3-(R25)-imidazolidin-2,
5-dione-yl, 4-(R25)-piperazine-2-one-yl, 4-(R25)-piperazine-2,6-dione-yl or 4-(R25)-1,4-diazepan-5-one-yl,
in which R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, Har1 is bonded to the parent molecular group via a ring carbon atom, and is pyridyl, thienyl, furanyl indolyl, benzothienyl, benzofuranyl, benzoxazolyl, benzothiazolyl, quinolyl or isoquinolyl, the enantiomers, as well as the salts of these compounds and enantiomers.

Further preferred compounds according to the present invention are those compounds of formula I in which A is ethylene or cyclopropylene, R1 is bonded to the 6-position of the imidazopyridine scaffold, and is phenyl, R2- and/or R3-substituted phenyl, or Har1, R11 is hydrogen, in which R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22, in which R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which Har2 is pyridyl, thienyl or furyl, R211 is 1-4C-alkyl, halogen, 1-4C-alkoxy, or mono- or di-1-4C-alkylamino, R212 is 1-4C-alkyl or halogen, R22 is hydrogen, hydroxy-2-4C-alkyl, 1-4C-alkoxy-2-4C-alkyl or 1-4C-alkyl, or R21 and R22 together and with inclusion of the nitrogen atom, to which they are bonded, form a heterocyclic ring Het1, in which Het1 is piperidinyl, pyrrolidinyl, azetidinyl, morpholinyl, thiomorpholinyl, S-oxo-thiomorpholinyl or S,S-dioxothiomorpholinyl, or indolinyl, isoindolinyl, 1,2,3,4-tetrahydroquinolinyl or 1,2,3,4-tetrahydroisoquinolinyl, or piperazinyl or homopiperazinyl, or 4N—(R25)-piperazinyl or 4N—(R25)-homopiperazinyl, 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl or 5-oxo-1,4-diazepanyl, 3-(R25)-imidazolidin-2-one-yl, 3-(R25)-imidazolidin-2,5-dione-yl, 4-(R25)-piperazine-2-one-yl, 4-(R25)-piperazine-2,6-dione-yl or 4-(R25)-1,4-diazepan-5-one-yl, in which R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, Har1 is bonded to the parent molecular group via a ring carbon atom, and is pyridyl, thienyl, furanyl indolyl, benzothienyl, benzofuranyl, benzoxazolyl, benzothiazolyl, quinolyl or isoquinolyl, the enantiomers, as well as the salts of these compounds and enantiomers.

Further preferred compounds according to the present invention are those compounds of formula I in which A is ethylene, R1 is bonded to the 6-position of the imidazopyridine scaffold, and is phenyl, or R2- and/or R3-substituted phenyl, R11 is hydrogen, in which R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, or phenyl-1-4C-alkoxy, R3 is hydrogen, 1-4C-alkyl, halogen, trifluoromethyl, 1-4C-alkoxy, or completely or predominantly fluorine-substituted 1-4C-alkoxy, the enantiomers, as well as the salts of these compounds and enantiomers.

Further preferred compounds according to the present invention are those compounds of formula I in which A is ethylene, R1 is bonded to the 6-position of the imidazopyridine scaffold, and is R2- and/or R3-substituted phenyl, R11 is hydrogen, in which R2 is —SO$_2$—N(R21)R22, in which R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which Har2 is pyridyl, thienyl or furyl, R211 is 1-4C-alkyl, halogen, 1-4C-alkoxy, or mono- or di-1-4C-alkylamino, R212 is 1-4C-alkyl or halogen, R22 is hydrogen, hydroxy-2-4C-alkyl, 1-4C-alkoxy-2-4C-alkyl or 1-4C-alkyl, or R21 and R22 together and with inclusion of the nitrogen atom, to which they are bonded, form a heterocyclic ring Het1, in which Het1 is piperidinyl, pyrrolidinyl, azetidinyl, morpholinyl, thiomorpholinyl, S-oxo-thiomorpholinyl or S,S-dioxothiomorpholinyl, or indolinyl, isoindolinyl, 1,2,3,4-tetrahydroquinolinyl or 1,2,3,4-tetrahydroisoquinolinyl, or piperazinyl or homopiperazinyl, or 4N—(R25)-piperazinyl or 4N—(R25)-homopiperazinyl, 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl or 5-oxo-1,4-diazepanyl, 3-(R25)-imidazolidin-2-one-yl, 3-(R25)-imidazolidin-2,5-dione-yl, 4-(R25)-piperazine-2-one-yl, 4-(R25)-piperazine-2,6-dione-yl or 4-(R25)-1,4-diazepan-5-one-yl, in which R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, the enantiomers, as well as the salts of these compounds and enantiomers.

Further preferred compounds according to the present invention are those compounds of formula I in which A is ethylene, R1 is bonded to the 6-position of the imidazopyridine scaffold, and is Har1, R11 is hydrogen, in which Har1 is bonded to the parent molecular group via a ring carbon atom, and is pyridyl, thienyl, furanyl, indolyl, benzothienyl, benzofuranyl, benzoxazolyl, benzothiazolyl, quinolyl or isoquinolyl, the enantiomers, as well as the salts of these compounds and enantiomers.

Further preferred compounds according to the present invention are those compounds of formula I in which A is 1-4C-alkylene, R1 is phenyl, R2-substituted phenyl or Har1, R11 is hydrogen, in which R2 is cyano, 1-4C-alkoxy or —SO$_2$—N(R21)R22, in which R21 is hydrogen, 1-4C-alkyl, Har2-1-4C-alkyl, phenyl or R211- and/or R212-substituted phenyl, in which Har2 is furyl or tetrahydrofuryl, R211 is 1-4C-alkyl or halogen, R212 is 1-4C-alkyl or halogen, R22 is hydrogen or 1-4C-alkyl, or R21 and R22 together and with inclusion of the nitrogen atom, to which they are bonded, form a heterocyclic ring Het1, in which Het1 is a 3- to 7-membered monocyclic fully saturated non-aromatic heterocyclic ring B, which heterocyclic ring B comprises one to three heteroatoms independently selected from nitrogen, oxygen and sulfur, and which ring Het1 is optionally substituted by R23 on a ring carbon atom, and/or which ring Het1 is optionally substituted by R25 on a ring nitrogen atom, in which R23 is 1-4C-alkyl, R25 is 1-4C-alkyl, Har1 is bonded to the parent molecular group via a ring carbon atom, and is a monocyclic or fused bicyclic 5- to 10-membered unsaturated heteroaryl radical comprising one to three heteroatoms, each of which is selected from a group consisting of nitrogen, oxygen and sulfur, the enantiomers, as well as the salts of these compounds and enantiomers.

Further preferred compounds according to the present invention are those compounds of formula I in which A is ethylene, R1 is phenyl, R2-substituted phenyl or Har1, R11 is hydrogen, in which R2 is cyano, 1-4C-alkoxy or —SO$_2$—N(R21)R22, in which R21 is hydrogen, 1-4C-alkyl, Har2-1-4C-alkyl or R211- and/or R212-substituted phenyl, in which Har2 is tetrahydrofuryl, R211 is 1-4C-alkyl or halogen, R212 is 1-4C-alkyl, R22 is hydrogen or 1-4C-alkyl, or R21 and R22 together and with inclusion of the nitrogen atom, to which they are bonded, form a heterocyclic ring Het1, in which Het1 is a 4- to 6-membered monocyclic fully saturated non-aromatic heterocyclic ring B, which heterocyclic ring B comprises one to three nitrogen atoms, and which ring Het1 is optionally substituted by R25 on a ring nitrogen atom, in which R25 is 1-4C-alkyl, Har1 is bonded to the parent molecular group via a ring carbon atom, and is a fused bicyclic 9-membered unsaturated heteroaryl radical comprising one oxygen atom, the enantiomers, as well as the salts of these compounds and enantiomers.

Further preferred compounds according to the present invention are those compounds of formula I in which A is ethylene, R1 is phenyl, R2-substituted phenyl or Har1, R11 is hydrogen, in which R2 is cyano, 1-4C-alkoxy or —SO$_2$—N(R21)R22, in which R21 is hydrogen, 1-4C-alkyl, Har2-1-4C-alkyl or R211- and/or R212-substituted phenyl, in which Har2 is tetrahydrofuryl, R211 is 1-4C-alkyl or halogen, R212 is 1-4C-alkyl, R22 is hydrogen or 1-4C-alkyl, or R21 and R22 together and with inclusion of the nitrogen atom, to which they are bonded, form a heterocyclic ring Het1, in which Het1 is an azetidinyl or piperazinyl ring, which ring Het1 is optionally substituted by R25 on a ring nitrogen atom, in which R25 is 1-4C-alkyl, Har1 is bonded to the parent molecular group via a ring carbon atom, and is a benzofuranyl ring, the enantiomers, as well as the salts of these compounds and enantiomers.

A special interest in the compounds according to the present invention refers to those compounds of this invention which are included—within the scope of this invention—by one or, when possible, a combination of more of the following embodiments:

One embodiment of the compounds of the present invention includes those compounds of formula I in which A is ethylene.

Another embodiment of the compounds of the present invention includes those compounds of formula I in which R11 is hydrogen.

Another special embodiment of the compounds of the present invention includes those compounds of formula I in which A is ethylene and R11 is hydrogen.

Another embodiment of the compounds of the present invention includes those compounds of formula I in which R1 is phenyl and A is ethylene and R11 is hydrogen.

Another embodiment of the compounds of the present invention includes those compounds of formula I in which R1 is R2- and/or R3-substituted phenyl and A is ethylene and R11 is hydrogen.

Another embodiment of the compounds of the present invention includes those compounds of formula I in which R1 is R2-substituted phenyl and A is ethylene and R11 is hydrogen.

Another embodiment of the compounds of the present invention includes those compounds of formula I in which R1 is Har1 and A is ethylene and R11 is hydrogen.

Another embodiment of the compounds of the present invention includes those compounds of formula I in which R1 is R4- and/or R5-substituted Har1 and A is ethylene and R11 is hydrogen.

Another embodiment of the compounds of the present invention includes those compounds of formula I in which R1 is bonded to the 6-position of the imidazopyridine ring system.

The substituents R2 and R3 of compounds according to this invention can be attached in the ortho, meta or para position with respect to the binding position in which the phenyl ring is bonded to the imidazopyridine ring system, whereby a special embodiment of the compounds of the present invention include those compounds of formula I in which R2 is attached in the meta or, particularly, para position.

In this context, another embodiment of the compounds of the present invention include those compounds of formula I in which R3 is attached in the ortho or meta position and R2 is attached in the para position with respect to the binding position in which the phenyl ring is bonded to the imidazopyridine ring system.

The compounds of formula I are chiral compounds having a chiral center in the binding position of the amino-azepinyl ring to the moiety A.

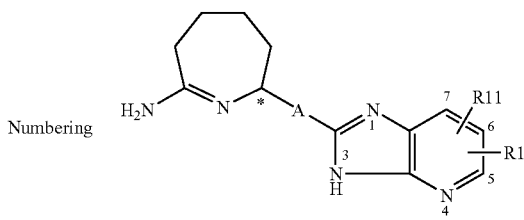

The invention includes all conceivable stereoisomers in pure form as well as in any mixing ratio including the racemates. In particular, the chiral center may have the absolute configuration R or the absolute configuration S (according to the rules of Cahn, Ingold and Prolog). A "pure stereoisomer" is to be understood as containing not more than 5 wt % of the other stereoisomer, preferably not more than 3 wt % and more preferably not more than 1 wt % of other stereoisomer.

The enantiomers can be separated in a manner known per se (for example by preparation and separation of appropriate diastereoisomeric compounds). Enantiomerically pure starting compounds or enantiomerically pure final compounds can be prepared via asymmetric syntheses; or by means of salt formation of the racemic compounds with optically active acids or bases, subsequent resolution of the salts and release of the desired compound from the salt. Enantiomerically pure starting compounds as well as enantiomerically pure compounds of the formula I can be also obtained from the racemates by chromatographic separation on chiral separating columns; by derivatization with chiral auxiliary reagents, subsequent diastereomer separation and removal of the chiral auxiliary group; or by (fractional) crystallization from a suitable solvent.

Compounds of formula I can be obtained as outlined in the following reaction schemes and described below or as specified by way of example in the following examples or similarly or analogously thereto.

In the following reaction schemes the synthesis of compounds of formula I, in which A is ethylene, is exemplarily described.

Thus, as shown in reaction scheme 1 below, compounds of formula IV, in which R11 has the meanings given above and X is a suitable leaving group, particularly iodine or, especially, bromine, is reacted with boronic acids or, particularly, boronic acid esters (e.g. pinacol esters) of formula Y-R1, in which R1 has the meanings given above and Y is a boronic acid group or, particularly, a boronic acid ester group, suitably a cyclic boronic acid ester group such as, for example, the boronic acid pinacol ester group, under conditions appropriate for a Suzuki reaction to occur to give corresponding compounds of formula III.

The Suzuki reaction can be carried out in a manner as described in the following examples or as known to the person skilled in the art in organic solvents alone, for example in toluene, benzene, dimethylformamide or in ethereal (e.g. dimethoxyethane or, in particular, dioxane) or alcohol solvents or in a mixture thereof, or preferably in a mixture comprising an organic solvent (in particular dioxane) and water, with organic (e.g. triethylamine) or preferably inorganic base (e.g. potassium hydroxide, thallium hydroxide, sodium bicarbonate, cesium carbonate, cesium fluoride or, in particular, potassium carbonate or sodium carbonate) in the presence of a transition metal catalyst, for example, a nickel or, in particular, palladium catalyst (e.g. $Pd(OAc)_2$, $PdCl_2(PPh_3)_2$ or $Pd(PPh_3)_4$, in particular, $PdCl_2(PCy_3)_2$ or $PdCl_2(dppf)$, Ac=acetyl, Ph=phenyl, Cy=cyclohexyl, dppf=1,1'-bis(diphenylphosphino)-ferrocene), and, optionally, lithium chloride, suitably at elevated temperature.

Boronic acids or boronic acid esters (e.g. pinacol esters) of formula R1-Y, in which R1 and Y have the meanings given above, are known or can be obtained in an art-known manner or analogously or similarly to known compounds. Boronic acid esters (e.g. pinacol esters) of formula R1-Y can be prepared, for example, starting from the corresponding triflates or, particularly, halides, preferably the bromides or iodides, which are art-known or which can be obtained according to art-known procedures, using e.g. bis-(pinacolato)-diboron in the presence of a transition metal, preferably palladium, catalyst. Optionally the boronic acid esters obtained can be isolated or, preferably, they are generated in situ and used in the subsequent Suzuki reaction without isolation.

The cyclic amide structure of compounds of formula III is converted into the cyclic amidine structure of compounds of formula I in a manner known to the person skilled in the art or as described in the following examples, e.g. via the thioamide structure of compounds of formula II (obtainable under suitable conditions with the aid of Lawesson's reagent) which is aminated with ammonia to give compounds of formula I.

Reaction Scheme 1:
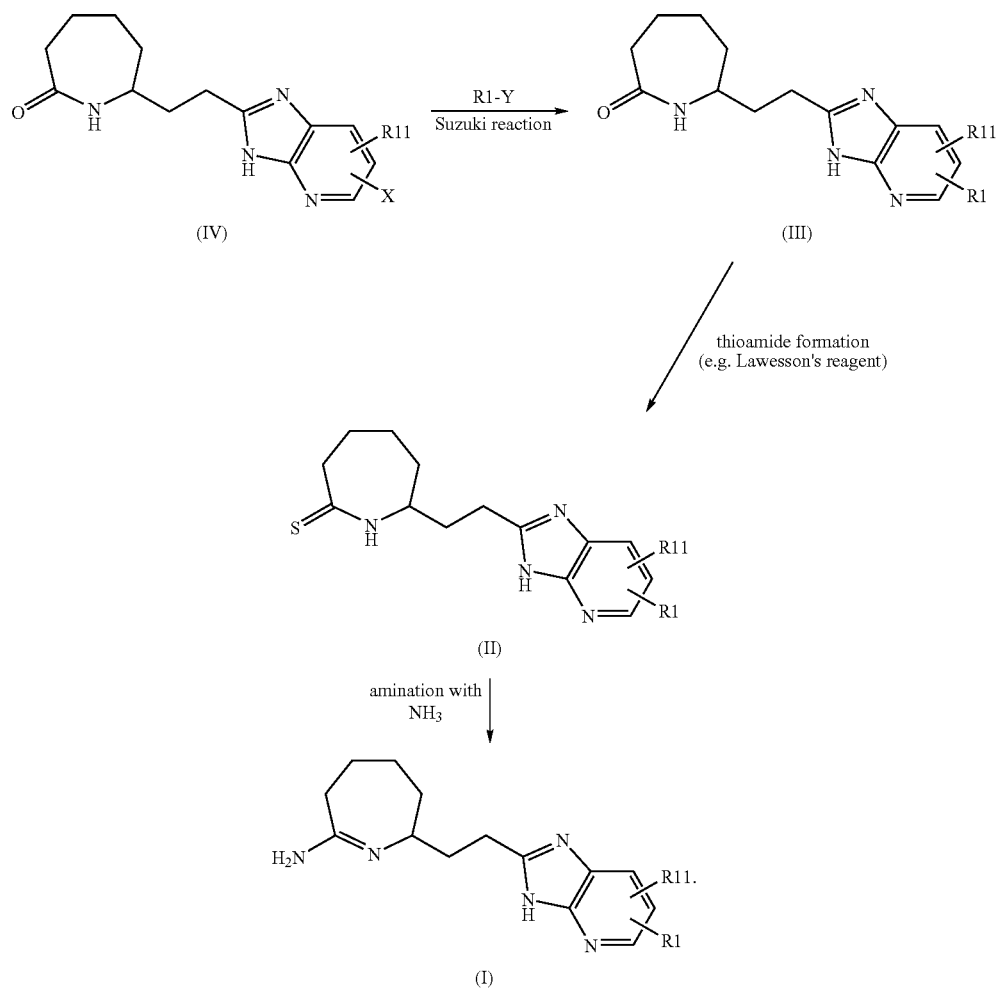
Reaction Scheme 2:
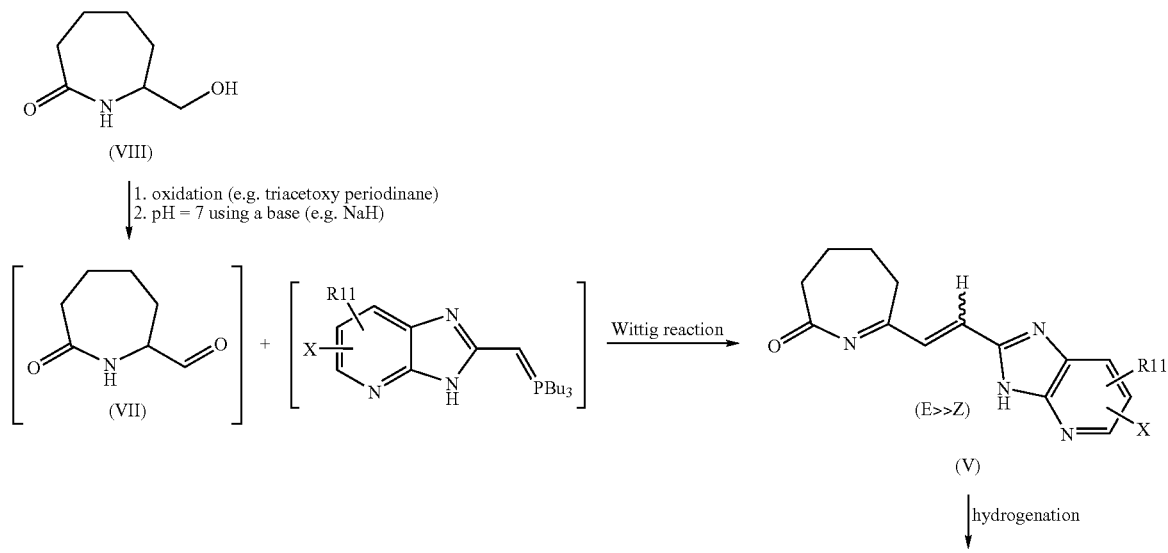

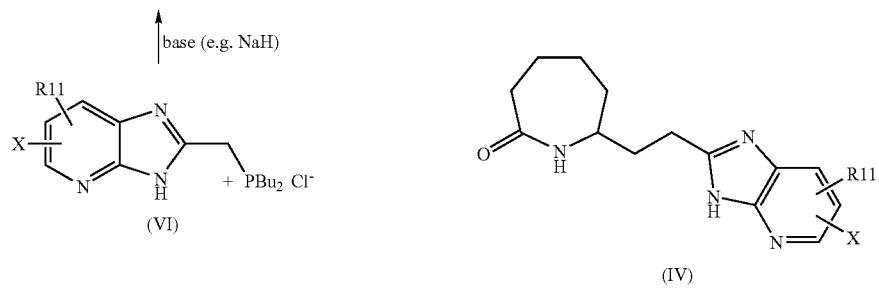

Compounds of formula IV, in which R11 and X have the meanings given above, are obtained as shown in reaction scheme 2.

In a Wittig reaction, compounds of formula VI, in which X and R11 have the meanings given above, are reacted with compounds of formula VII to give corresponding compounds of formula V. With regard to the configuration of the exocyclic double bond obtained by Wittig reaction, the outcome can be a Z- or, particularly, E-configurated product or, especially, a mixture thereof. Said reaction can be carried out in a manner as described in the following examples or as known to the person skilled in the art according to a Wittig reaction, in a suitable solvent such as, for example, methanol, tetrahydrofurane, toluene or a mixture thereof, using a suitable base such as, for example, sodium hydride or sodium methanolate, at room temperature or at elevated temperature.

The reduction of the abovementioned exocyclic double bond following the deprotection reaction leads to desired compounds of formula IV, in which X and R11 have the meanings given above. This reaction can be carried out as hydrogenation reaction according to procedures known to the person skilled in the art or according to the following examples in the presence of a suitable catalyst, such as, for example, palladium on active carbon or platinum dioxide, in a suitable solvent (e.g. in a lower alcohol, such as, for example, methanol). If necessary, acid, such as trifluoroacetic acid or acetic acid, can be added to the solvent.

Compounds of formula VI are obtained as shown in reaction scheme 3. In a first reaction step of reaction scheme 3, diamino compounds of formula X, in which X and R11 have the meanings indicated above, are converted into 3H-imidazo[4,5-b]pyridine derivatives in a manner known from the literature or with analogous or similar use of processes known from the literature. For example, said compounds of formula X can be reacted with carboxylic acids or carboxylic acid derivatives of formula Z1-CH$_2$-Z2, in which Z1 is a suitable leaving group, advantageously chlorine, and Z2 is a carboxyl or, particularly, cyano radical, to give in a condensation reaction compounds of formula IX, in which R1, X and Z1 have the meanings mentioned above. This condensation reaction can be carried out as known to one of ordinary skill in the art or as described by way of example in the following examples, for example, by using a suitable condensing agent such as preferably polyphosphoric acid in a suitable inert solvent or, preferably, without further solvent using an excess of condensing agent, preferably at elevated temperature.

Reaction scheme 3:

As shown in reaction scheme 3, compounds of formula IX can be converted with certain phosphanes into corresponding phosphonium salts which can be used in the abovementioned Wittig reaction. Preferably, compounds of formula IX are reacted with triphenylphosphane (R=phenyl) or, particularly, tributylphosphane (R=butyl) to give corresponding compounds of formula VI. Said reaction can be carried out in a manner habitual per se or as described in the following examples in a suitable solvent such as, for example, acetonitrile or N,N-dimethylformamide or a mixture thereof, at elevated temperature, optionally in the presence of an auxiliary such as tetrabutylammonium iodide.

Compounds of formula X are known or can be obtained according to known procedures (see e.g. S.-X. Cai et al., J. Med. Chem. 1997, 40(22), 3679-3686).

Compounds of formula VII are obtained as shown in reaction scheme 2 or 4 by oxidation of compounds of formula XI or VIII, respectively. Optionally compounds of formula VII obtained can be isolated or, preferably, they are generated in situ and used in the subsequent Wittig reaction without isolation.

Compounds of formula XI can be obtained as outlined in reaction scheme 4 according to known procedures (see e.g. L. Benati et al., J. Org. Chem. 1999, 64(21), 7836-7841 and L. Benati et al., J. Org. Chem. 1999, 64(14), 5132-5138) or as described in the following examples via a modified Schmidt rearrangement and subsequent reduction of the ester group.

Reaction scheme 4:

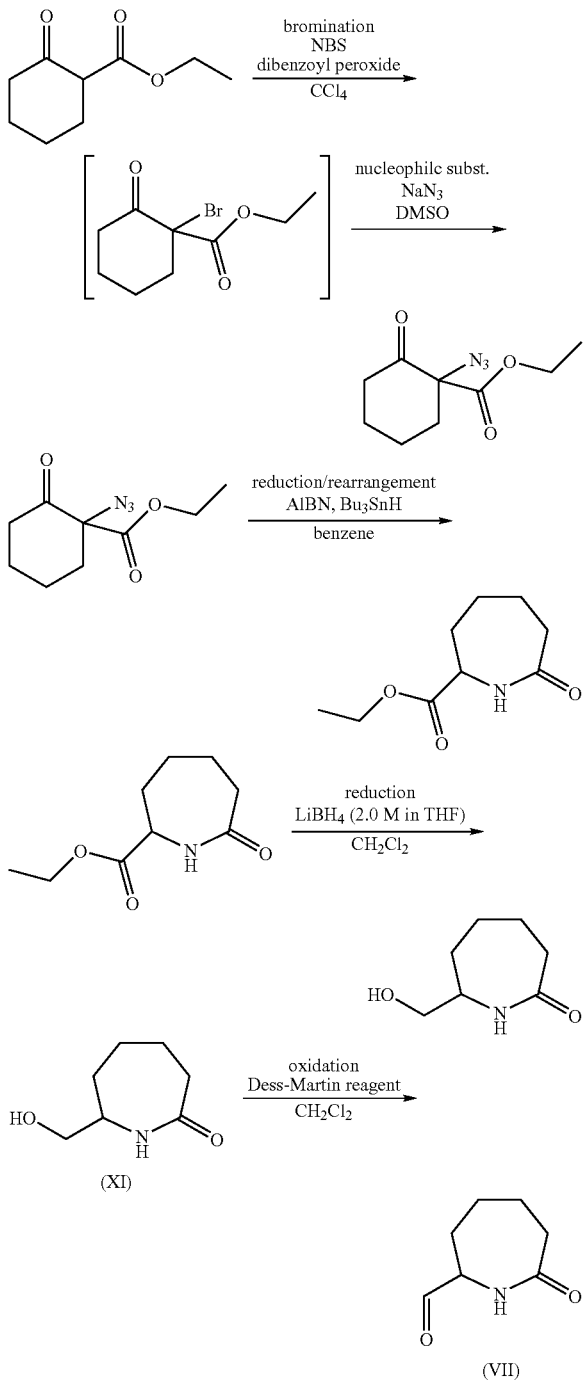

Optionally, compounds of formula I can be converted into their salts, or, optionally, salts of the compounds of formula I can be converted into the free compounds. Corresponding processes are known to the person skilled in the art.

It is known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3$^{rd}$ Ed, or in P. Kocienski, Protecting Groups, Thieme Medical Publishers, 2000.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basi-fication into the free compounds which, in turn, can be converted into salts. In this manner, pharma-cologically non-tolerable salts can be converted into pharmacologically tolerable salts.

Suitably, the conversions mentioned in this invention can be carried out analogously or similarly to methods which are familiar per se to the person skilled in the art, for example, in the manner which is described by way of example in the following examples.

The person skilled in the art knows on the basis of his/her knowledge and on the basis of those synthesis routes, which are shown and described within the description of this invention, how to find other possible synthesis routes for compounds according to this invention: All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicit, implicit or inherent disclosure) of the present invention without departing from the spirit and scope of this invention as defined by the scope of the appended claims.

The following examples illustrate the invention in greater detail, without restricting it. As well, further compounds according to the present invention, of which the preparation is explicitly not described, can be prepared in an analogous way or in a way which is known by a person skilled in the art using customary preparation methods and process techniques.

Any or all of the compounds, which are mentioned in the examples as final compounds as well as their salts are a preferred subject of the invention.

EXAMPLES

In the examples, m.p. stands for melting point, h for hours, d for days, min for minutes, TLC for thin layer chromatography, Rf for retention factor, MS for mass spectrum, M for molecular ion, ESI-MS for electrospray ionization mass spectrometry, LC-MS for liquid chromatography coupled to mass spectrometry, Lawesson's reagent for 2,4-bis(4-methoxyphenyl)-1,3-dithia-2,4-diphosphetane-2,4-disulfide, dppf/DPPF for 1,1'-bis(diphenylphosphino)-ferrocene, Hünig's base for N,N-diisopropylethylamine. Other abbreviations have their meanings customary per se for the skilled person. LiChroprep-NH$_2$® (25-40 µm) is available from Merck KGaA (Darmstadt, Germany). Percentages given for molecular ion peaks in the ESI-MS refer to the intensity of each signal due to a halogen (Br, Cl) isotope ratio.

Final Products

1. 7-[2-(6-Phenyl-3H-imidazo[4,5-b]pyridin-2-yl)-ethyl]-4,5,6,7-tetrahydro-3H-azepin-2-ylamine 65 mg of 7-[2-(6-phenyl-3H-imidazo[4,5-b]pyridin-2-yl)-ethyl]-azepan-2-thione (compound A1) are suspended in 4.3 ml of methanol containing ammonia (strength: 7.0 M) and heated at 50° C. for 90 hours. Subsequently, the reaction mixture is evaporated to dryness and purified by flash chromatography on LiChroprep-NH$_2$® (eluent gradient: dichloromethane/0-100 vol. % methanol), and lyophilized from 2.0 ml of water, 5.0 ml of dioxane to afford 29.5 mg of the title compound as an amorphous, colorless solid of m.p. 117° C. (decomp.). ESI-MS: 334.3 (MH$^+$). TLC: Rf=0.35 (LiChroprep-NH$_2$® HPTLC, methanol/water 10:1 parts by volume).

2. 7-[2-(6-{4-Cyano-phen-1-yl}-3H-imidazo[4,5-b]pyridin-2-yl)-ethyl]-4,5,6,7-tetrahydro-3H-azepin-2-ylamine The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 90 mg of 7-[2-(6-{4-cyano-phen-1-yl}-3H-imidazo[4,5-b]pyridin-2-yl)-ethyl]-azepan-2-thione (compound A2) and 5.5 ml of methanol containing ammonia (strength: 7.0 M) at 50° C. for 90 hours. Purification by flash chromatography on LiChroprep-NH$_2$® (eluent gradient: dichloromethane/0-100 vol. % methanol) affords 43.3 mg of the title compound as an amorphous solid of m.p. 175° C. (decomp.). ESI-MS: 359.2 (MH$^+$). TLC: Rf=0.33 (LiChroprep-NH$_2$® HPTLC, methanol/water 10:1 parts by volume).

3. 7-{2-[6-(4-Methoxy-phenyl)-3H-imidazo[4,5-b]pyridin-2-yl]-ethyl}-4,5,6,7-tetrahydro-3H-azepin-2-ylamine The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 98 mg of 7-{2-[6-(4-methoxy-phenyl)-3H-imidazo[4,5-b]pyridin-2-yl]-ethyl}-azepane-2-thione (compound A3) and 6.0 ml of methanol containing ammonia (strength: 7.0 M) at 50° C. for 5 days. Purification by flash chromatography on LiChroprep-NH$_2$® (eluent: ethanol) affords 23 mg of the title compound as an amorphous, colorless solid of m.p. 306° C. ESI-MS: 364.2 (MH$^+$). TLC: Rf=0.50 (LiChroprep-NH$_2$® HPTLC, methanol/water 10:1 parts by volume).

4. 7-[2-(6-Benzofuran-2-yl-3H-imidazo[4,5-b]pyridin-2-yl)-ethyl]-4,5,6,7-tetrahydro-3H-azepin-2-ylamine The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 85 mg of 7-[2-(6-benzofuran-2-yl-3H-imidazo[4,5-b]pyridin-2-yl)-ethyl]-azepane-2-thione (compound A4) and 5.0 ml of methanol containing ammonia (strength: 7.0 M) at 50° C. for 70 hours. Purification by flash chromatography on LiChroprep-NH$_2$® (eluent gradient: ethyl acetate/0-100 vol. % 2-propanol; then: neat methanol) affords 40.4 mg of the title compound as a waxy solid. ESI-MS: 374.2 (MH$^+$). TLC: Rf=0.21 (LiChroprep-NH$_2$® HPTLC, neat methanol).

5. 4-{2-[2-(7-Amino-3,4,5,6-tetrahydro-2H-azepin-2-yl)-ethyl]-3H-imidazo[4,5-b]pyridin-6yl}-N,N-dimethyl-benzenesulfonamide The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 50 mg of N,N-dimethyl-4-{2-[2-(7-thioxo-azepan-2-yl)-ethyl]-3H-imidazo[4,5-b]pyridin-6-yl}-benzenesulfonamide (compound A5) and 2.53 ml of methanol containing ammonia (strength: 7.0 M) at 50° C. for 65 hours. Purification by flash chromatography on LiChroprep-NH$_2$® (eluent: dichloromethane/0-10 vol. % methanol) and lyophilisation from dioxane/water (10:1 parts by volume) afford 32 mg of the title compound as an amorphous, colorless solid of m.p. 195° C. (decomp.). ESI-MS: 441.2 (MH$^+$). TLC: Rf=0.44 (LiChroprep-NH$_2$® HPTLC, methanol/water 10:1 parts by volume).

6. 7-(2-{6-[4-(Azetidine-1-sulfonyl)-phenyl]-3H-imidazo[4,5-b]pyridin-2-yl}-ethyl)-4,5,6,7-tetrahydro-3H-azepin-2-ylamine The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 92 mg of 7-(2-{6-[4-(azetidine-1-sulfonyl)-phenyl]-3H-imidazo[4,5-b]pyridin-2-yl}-ethyl)-azepane-2-thione (compound A6) and 4.50 ml of methanol containing ammonia (strength: 7.0 M) at 50° C. for 70 hours. Purification by flash chromatography on LiChroprep-NH$_2$® (eluent gradient: dichloromethane/0-100 vol. % methanol) affords 56 mg of the title compound as an amorphous solid of m.p. 154° C. (decomp.). ESI-MS: 453.2 (MH$^+$). TLC: Rf=0.23 (LiChroprep-NH$_2$® HPTLC, neat methanol).

7. 7-(2-{6-[4-(4-Ethyl-piperazine-1-sulfonyl)-phenyl]-3H-imidazo[4,5-b]pyridin-2-yl}-ethyl)-4,5,6,7-tetrahydro-3H-azepin-2-ylamine The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 157 mg of 7-(2-{6-[4-(4-ethyl-piperazine-1-sulfonyl)-phenyl]-3H-imidazo[4,5-b]pyridin-2-yl}-ethyl)-azepane-2-thione (compound A7) and 6.90 ml of methanol containing ammonia (strength: 7.0 M) at 50° C. for 90 hours. Purification by flash chromatography on LiChroprep-NH$_2$® (eluent gradient: ethyl acetate/0-100 vol. % 2-propanol) affords 28 mg of the title compound as an amorphous solid of m.p. 199° C. ESI-MS: 528.2 (MNH$_4^+$), 510.4 (MH$^+$), TLC: Rf=0.30 (LiChroprep-NH$_2$® HPTLC, neat methanol).

8. 4-{2-[2-(7-Amino-3,4,5,6-tetrahydro-2H-azepin-2-yl)-ethyl]-3H-imidazo[4,5-b]pyridin-6-yl}-N-(2-fluoro-4-methyl-phenyl)-benzenesulfonamide The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 100 mg of N-(2-fluoro-4-methyl-phenyl)-4-{2-[2-(7-thioxo-azepan-2-yl)-ethyl]-3H-imidazo[4,5-b]pyridin-6-yl}-benzenesulfonamide (compound A8) and 4.30 ml of methanol containing ammonia (strength: 7.0 M) at 50° C. for 90 hours. Subsequently, the mixture is filtered with suction. The residue is washed with 20 ml of methanol and dried under high vacuum to afford 61 mg of the pure title compound as an amorphous, colorless solid of m.p. 265° C. ESI-MS: 521.2 (MH$^+$), TLC: Rf=0.28 (HPTLC RP-C18; acetonitrile/water 2:1 parts by volume).

9. 4-{2-[2-(7-Amino-3,4,5,6-tetrahydro-2H-azepin-2-yl)-ethyl]-3H-imidazo[4,5-b]pyridin-6-yl}-N-o-tolyl-benzenesulfonamide The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 71 mg of 4-{2-[2-(7-thioxo-azepan-2-yl)-ethyl]-3H-imidazo[4,5-b]pyridin-6-yl}-N-o-tolyl-benzenesulfonamide (compound A9) and 3.2 ml of methanol containing ammonia (strength: 7.0 M) at 50° C. for 66 hours. Subsequently, the solution is concentrated in vacuo to yield 60 mg of the pure title compound as an amorphous, colorless solid of m.p. 215° C. ESI-MS: 503.4 (MH$^+$), TLC: Rf=0.25 (HPTLC RP-C18; acetonitrile/water 2:1 parts by volume).

10. 4-{2-[2-(7-Amino-3,4,5,6-tetrahydro-2H-azepin-2-yl)-ethyl]-3H-imidazo[4,5-b]pyridin-6-yl}-N-methyl-N-(tetrahydro-furan-2-ylmethyl)-benzenesulfonamide The title compound is synthesized as described for 7-[2-(6-phenyl-3H-imidazo[4,5-b]pyridin-2-yl)-ethyl]-4,5,6,7-tetrahydro-3H-azepin-2-ylamine (compound 1) from 114 mg of N-methyl-N-(tetrahydro-furan-2-ylmethyl)-4-{2-[2-(7-thioxo-azepan-2-yl)-ethyl]-3H-imidazo[4,5-b]pyridin-6-yl}-benzenesulfonamide (compound A10) and 5.0 ml of methanol containing ammonia (strength: 7.0 M) at 50° C. for 64 hours. Purification by flash chromatography on RP-C8 resin (eluent: acetonitrile/water 2:1 parts by volume) and lyophilization from 1.0 ml of water and 3.0 ml of dioxane afford 14 mg of the title compound as an amorphous, colorless solid of m.p. 260° C. ESI-MS: 511.4 (MH$^+$). TLC: Rf=0.17 (HPTLC RP-C18, acetonitrile/water 2:1 parts by volume).

Starting Materials:

A1. 7-[2-(6-Phenyl-3H-imidazo[4,5-b]pyridin-2-yl)-ethyl]-azepan-2-thione 90 mg of 7-[2-(6-phenyl-3H-imidazo[4,5-b]pyridin-2-yl)-ethyl]-azepan-2-one (compound B1) are dissolved in 10 ml of toluene under an atmosphere of dry nitrogen. Subsequently, 144 mg of Lawesson's reagent are added and the solution is heated at 100° C. for 17 hours. Thereafter, the reaction mixture is evaporated to dryness to yield approximately 200 mg of crude material, which is purified by chromatography on basic aluminum oxide (eluent: dichloromethane) to afford 71 mg of the title compound as a light yellow, waxy solid. ESI-MS: 351.2 (MH$^+$). TLC: Rf=0.53 (dichloromethane/ethanol 10:1 parts by volume).

A2. 7-[2-(6-{4-Cyano-phen-1-yl}-3H-imidazo[4,5-b]pyridin-2-yl)-ethyl]-azepan-2-thione 120 mg of 7-[2-(6-{4-cyano-phen-1-yl}-3H-imidazo[4,5-b]pyridin-2-yl)-ethyl]-azepan-2-one (compound B2) are suspended in 30 ml of dry dioxane under an atmosphere of nitrogen. Subsequently, 142 mg of Lawesson's reagent are added and the solution is heated at 100° C. for 17 hours. Thereafter, the reaction mixture is evaporated to dryness to yield approximately 300 mg of crude material, which is purified by chromatography on flash silica gel (eluent gradient: dichloromethane/0-5 vol. % ethanol) to afford 100 mg of the title compound as a light yellow, waxy solid. ESI-MS: 376.2 (MH$^+$). TLC: Rf=0.38 (dichloromethane/ethanol 10:1 parts by volume).

A3. 7-{2-[6-(4-Methoxy-phenyl)-3H-imidazo[4,5-b]pyridin-2-yl]-ethyl}-azepane-2-thione The title compound is synthesized as described for 7-[2-(6-{4-cyano-phen-1-yl}-3H-imidazo[4,5-b]pyridin-2-yl)-ethyl]-azepan-2-thione (compound A2) from 120 mg of 7-{2-[6-(4-methoxy-phenyl)-3H-imidazo[4,5-b]pyridin-2-yl]-ethyl}-azepan-2-one (compound B3) and 222 mg of Lawesson's reagent. Purification by chromatography on flash silica gel (eluent gradient: dichloromethane/0-10 vol. % ethanol) affords 104 mg of the title compound as a light yellow, waxy solid. ESI-MS: 381.2 (MH$^+$). TLC: Rf=0.64 (dichloromethane/ethanol 10:1 parts by volume).

A4. 7-[2-(6-Benzofuran-2-yl-3H-imidazo[4,5-b]pyridin-2-yl)-ethyl]-azepane-2-thione The title compound is synthesized as described for 7-[2-(6-{4-cyano-phen-1-yl}-3H-imidazo[4,5-b]pyridin-2-yl)-ethyl]-azepan-2-thione (compound A2) from 100 mg of 7-[2-(6-benzofuran-2-yl-3H-imidazo[4,5-b]pyridin-2-yl)-ethyl]-azepan-2-one (compound B4) and 110 mg of Lawesson's reagent. Purification by chromatography on flash silica gel (eluent gradient: dichloromethane/0-20 vol. % ethanol) yields 82 mg of the title compound as a light yellow, waxy solid. ESI-MS: 391.2 (MH$^+$). TLC: Rf=0.55 (dichloromethane/ethanol 10:1 parts by volume).

A5. N,N-Dimethyl-4-{2-[2-(7-thioxo-azepan-2-yl)-ethyl]-3H-imidazo[4,5-b]pyridin-6-yl}-benzenesulfonamide The title compound is synthesized as described for 7-[2-(6-{4-cyano-phen-1-yl}-3H-imidazo[4,5-b]pyridin-2-yl)-ethyl]-azepan-2-thione (compound A2) from 85 mg of N,N-dimethyl-4-{2-[2-(7-oxo-azepan-2-yl)-ethyl]-3H-imidazo[4,5-b]pyridin-6-yl}-benzenesulfonamide (compound B5) and 82 mg of Lawesson's reagent. Purification by chromatography on flash silica gel (eluent gradient: dichloromethane/0-5 vol. % ethanol) affords 56 mg of the title compound as a light yellow, waxy solid. ESI-MS: 458.3 (MH$^+$). TLC: Rf=0.46 (dichloromethane/ethanol 10:1 parts by volume).

A6. 7-(2-{6-[4-(Azetidine-1-sulfonyl)-phenyl]-3H-imidazo[4,5-b]pyridin-2-yl}-ethyl)-azepane-2-thione The title compound is synthesized as described for 7-[2-(6-{4-cyano-phen-1-yl}-3H-imidazo[4,5-b]pyridin-2-yl)-ethyl]-azepan-2-thione (compound A2) from 258 mg of 7-(2-{6-[4-(azetidine-1-sulfonyl)-phenyl]-3H-imidazo[4,5-b]pyridin-2-yl}-ethyl)-azepan-2-one (compound B6) and 242 mg of Lawesson's reagent. Purification by chromatography on flash silica gel (eluent gradient: dichloromethane/0-5 vol. % ethanol) affords 99 mg of the title compound as a beige

A7. 7-(2-{6-[4-(4-Ethyl-piperazine-1-sulfonyl)-phenyl]-3H-imidazo[4,5-b]pyridin-2-yl}-ethyl)-azepane-2-thione The title compound is analogously synthesized as described for 7-[2-(6-{4-cyano-phen-1-yl}-3H-imidazo[4,5-b]pyridin-2-yl)-ethyl]-azepan-2-thione (compound A2) from 170 mg of 7-(2-{6-[4-(4-ethyl-piperazine-1-sulfonyl)-phenyl]-3H-imidazo[4,5-b]pyridin-2-yl}-ethyl)-azepan-2-one (compound B7) and 142 mg of Lawesson's reagent at 100° C. for 2.5 hours in 20 ml of dioxane. Purification by chromatography on flash silica gel (eluent gradient: dichloromethane/0-10 vol. % ethanol) affords 163 mg of the title compound as a waxy solid. ESI-MS: 527.3 (MH$^+$). TLC: Rf=0.34 (dichloromethane/ethanol 10:1 parts by volume).

A8. N-(2-Fluoro-4-methyl-phenyl)-4-{2-[2-(7-thioxo-azepan-2-yl)-ethyl]-3H-imidazo[4,5-b]pyridin-6-yl}-benzenesulfonamide The title compound is analogously synthesized as described for 7-[2-(6-{4-cyano-phen-1-yl}-3H-imidazo[4,5-b]pyridin-2-yl)-ethyl]-azepan-2-thione (compound A2) from 180 mg of N-(2-fluoro-4-methyl-phenyl)-4-{2-[2-(7-oxo-azepan-2-yl)-ethyl]-3H-imidazo[4,5-b]pyridin-6-yl}-benzenesulfonamide (compound B8) and 146 mg of Lawesson's reagent at 100° C. for 3 hours in 20 ml of dioxane. Purification by chromatography on flash silica gel (eluent gradient: dichloromethane/0-10 vol. % ethanol) affords 106 mg of the title compound as a colorless solid of m.p. 271° C. ESI-MS: 538.2 (MH$^+$). TLC: Rf=0.40 (dichloromethane/ethanol 10:1 parts by volume).

A9. 4-{2-[2-(7-Thioxo-azepan-2-yl)-ethyl]-3H-imidazo[4,5-b]pyridin-6-yl}-N-o-tolyl-benzenesulfonamide The title compound is analogously synthesized as described for 7-[2-(6-{4-cyano-phen-1-yl}-3H-imidazo[4,5-b]pyridin-2-yl)-ethyl]-azepan-2-thione (compound A2) from 88 mg of 4-{2-[2-(7-oxo-azepan-2-yl)-ethyl]-3H-imidazo[4,5-b]pyridin-6-yl}-N-o-tolyl-benzenesulfonamide (compound B9) and 77 mg of Lawesson's reagent. Purification by chromatography on LiChroprep-NH$_2$® (eluents: i. neat dichloromethane, ii. dichloromethane/ethanol 20:1 parts by volume) affords 78 mg of the title compound as a waxy solid. ESI-MS: 520.4 (MH$^+$). TLC: Rf=0.44 (LiChroprep-NH$_2$® HPTLC, dichloromethane/ethanol 10:1 parts by volume).

A10. N-Methyl-N-(tetrahydro-furan-2-ylmethyl)-4-{2-[2-(7-thioxo-azepan-2-yl)-ethyl]-3H-imidazo[4,5-b]pyridin-6-yl}-benzenesulfonamide The title compound is synthesized as described for 7-[2-(6-{4-cyano-phen-1-yl}-3H-imidazo[4,5-b]pyridin-2-yl)-ethyl]-azepan-2-thione (compound A2) from 125 mg of N-methyl-4-{2-[2-(7-oxo-azepan-2-yl)-ethyl]-3H-imidazo[4,5-b]pyridin-6-yl}-N-(tetrahydro-furan-2-ylmethyl)-benzenesulfonamide (compound B10) and 104 mg of Lawesson's reagent. Purification by chromatography on flash silica gel (eluent gradient: dichloromethane/0-10 vol. % ethanol) affords 123 mg of the title compound as a waxy solid. ESI-MS: 528.9 (MH$^+$). TLC: Rf=0.43 (dichloromethane/ethanol 10:1 parts by volume).

B1. 7-[2-(6-Phenyl-3H-imidazo[4,5-b]pyridin-2-yl)-ethyl]-azepan-2-one 100 mg of 7-[2-(6-bromo-3H-imidazo[4,5-b]pyridin-2-yl)-ethyl]-azepan-2-one (compound C1) are dissolved in 8.0 ml of oxygen free dioxane under an atmosphere of nitrogen. Subsequently, 900 µl of aqueous sodium carbonate solution (strength 2.0 M), 72 mg of commercially available 2-phenyl-1,3,2-dioxoborinane, and 26 mg of trans-dichloro-bis(tricyclohexyl-phosphine)-palladium(II) are added. The reaction mixture is stirred at 110° C. for 96 hours. Thereafter, the mixture is evaporated to dryness and purified by chromatography on basic aluminum oxide (eluent: dichloromethane) to yield 95 mg of the title compound as a light yellow oil. ESI-MS: 335.3 (MH$^+$). TLC: Rf=0.24 (dichloromethane/ethanol 10:1 parts by volume).

B2. 7-[2-(6-{4-Cyano-phen-1-yl}-3H-imidazo[4,5-b]pyridin-2-yl)-ethyl]-azepan-2-one The title compound is synthesized as described for 7-[2-(6-phenyl-3H-imidazo[4,5-b]pyridin-2-yl)-ethyl]-azepan-2-one (compound B1) from 300 mg of 7-[2-(6-bromo-3H-imidazo[4,5-b]pyridin-2-yl)-ethyl]-azepan-2-one (compound C1), 2.67 ml of aqueous sodium carbonate solution (strength 2.0 M), 306 mg of commercially available 4-(4,4,5,5-tetramethyl-1,3,2-dioxaborolan-2-yl)benzonitrile, and 81 mg of trans-dichloro-bis(tricyclohexyl-phosphine)-palladium(II) at 110° C. for 40 hours. Purification by chromatography on flash silica gel (eluent gradient: dichloromethane/0-10 vol. % ethanol) yields 129 mg of the title compound as a waxy solid. ESI-MS: 360.2 (MH$^+$). TLC: Rf=0.27 (dichloromethane/ethanol 10:1 parts by volume).

B3. 7-[2-{6-(4-Methoxy-phenyl)-3H-imidazo[4,5-b]pyridin-2-yl]-ethyl}-azepan-2-one The title compound is synthesized as described for 7-[2-(6-phenyl-3H-imidazo[4,5-b]pyridin-2-yl)-ethyl]-azepan-2-one (compound B1) from 100 mg of 7-[2-(6-bromo-3H-imidazo[4,5-b]pyridin-2-yl)-ethyl]-azepan-2-one (compound C1), 677 µl of aqueous sodium carbonate solution (strength 2.0 M), 52 mg of commercially available 4-methoxyphenyl-boronic acid, and 72 mg of trans-dichloro-bis(tricyclohexyl-phosphine)-palladium(II) at 110° C. for 96 hours. Purification by chromatography on flash silica gel (eluent gradient: dichloromethane/0-20 vol. % ethanol) yields 99 mg of the title compound as a waxy solid. ESI-MS: 365.2 (MH$^+$). TLC: Rf=0.32 (dichloromethane/ethanol 10:1 parts by volume).

B4. 7-[2-(6-Benzofuran-2-yl-3H-imidazo[4,5-b]pyridin-2-yl)-ethyl]-azepan-2-one The title compound is synthesized as described for 7-[2-(6-phenyl-3H-imidazo[4,5-b]pyridin-2-yl)-ethyl]-azepan-2-one (compound B1) from 300 mg of 7-[2-(6-bromo-3H-imidazo[4,5-b]pyridin-2-yl)-ethyl]-azepan-2-one (compound C1), 2.67 ml of aqueous sodium carbonate solution (strength 2.0 M), 651 mg of commercially available benzo[b]furan-2-boronic acid, and 135 mg of trans-dichloro-bis(tricyclohexyl-phosphine)-palladium(II) at 110° C. for 6 days. Purification by chromatography on flash silica gel (eluent gradient: dichloromethane/5-20 vol. % ethanol) yields 160 mg of the title compound as an amorphous solid of m.p. 215° C. ESI-MS: 375.9 (MH$^+$). TLC: Rf=0.26 (dichloromethane/ethanol 10:1 parts by volume).

B5. N,N-Dimethyl-4-{2-[2-(7-oxo-azepan-2-yl)-ethyl]-3H-imidazo[4,5-b]pyridin-6-yl}-benzenesulfonamide The title compound is analogously synthesized as described for 7-[2-(6-phenyl-3H-imidazo[4,5-b]pyridin-2-yl)-ethyl]-azepan-2-one (compound B1) from 100 mg of 7-[2-(6-bromo-3H-imidazo[4,5-b]pyridin-2-yl)-ethyl]-azepan-2-one (compound C1), 890 µl of aqueous sodium carbonate solution (strength 2.0 M), 138 mg N,N-dimethyl-4-(4,4,5,5-tetramethyl-[1,3,2]dioxaborolan-2-yl)-benzenesulfonamide (compound C2), and 26 mg of trans-dichloro-bis(tricyclohexyl-phosphine)-palladium(II) at 160° C. for 30 min (microwave irradiation, power ≦300 W). Purification by chromatography on flash silica gel (eluent gradient: dichloromethane/0-10 vol. % ethanol) yields 93 mg of the title compound as a waxy solid. ESI-MS: 442.4 (MH$^+$). TLC: Rf=0.41 (dichloromethane/ethanol 10:1 parts by volume).

B6. 7-(2-{6-[4-(Azetidine-1-sulfonyl)-phenyl]-3H-imidazo[4,5-b]pyridin-2-yl}-ethyl)-azepan-2-one 378 mg of 1-(4-bromo-benzenesulfonyl)-azetidine (compound C3) are dissolved in 10 ml of oxygen-free dioxane under an atmosphere of dry nitrogen. Subsequently, 383 mg of bis(pinacolato)diboron, 30 mg of Pd(Cl)$_2$(dppf).CH$_2$Cl$_2$, 23 mg of DPPF (1,1'-bis(diphenylphosphino)-ferrocene), and 403 mg of potassium acetate are added. The reaction mixture is heated at 110° C. for 16 hours during which time the former yellowish suspension becomes black (LC-MS monitoring for boronic ester intermediate). Thereafter, 300 mg of 7-[2-(6-bromo-3H-imidazo[4,5-b]pyridin-2-yl)-ethyl]-azepan-2-one (compound C1), 2.70 ml of aqueous sodium carbonate solution (strength 2.0 M), and 66 mg of trans-dichloro-bis(tricyclohexyl-phosphine)-palladium(II) are added and the reaction mixture is heated at 110° C. for 72 hours. Subsequently, the mixture is diluted with 50 ml of water and extracted three times each with 100 ml of dichloromethane. The organic layer is separated, dried using Na$_2$SO$_4$ (solid) and concentrated in vacuo. The resulting crude material is purified by chromatography on flash silica gel (eluent gradient: dichloromethane/0-10 vol. % ethanol) to yield 187 mg of the title compound as an oil. ESI-MS: 454.2 (MH$^+$). TLC: Rf=0.29 (dichloromethane/ethanol 10:1 parts by volume).

B7. 7-(2-{6-[4-(4-Ethyl-piperazine-1-sulfonyl)-phenyl]-3H-imidazo[4,5-b]pyridin-2-yl}-ethyl)-azepan-2-one The title compound is analogously synthesized as described for 7-[2-(6-phenyl-3H-imidazo[4,5-b]pyridin-2-yl)-ethyl]-azepan-2-one (compound B1) from 300 mg of 7-[2-(6-bromo-3H-imidazo[4,5-b]pyridin-2-yl)-ethyl]-azepan-2-one (compound C1), 2.67 ml of aqueous sodium carbonate solution (strength 2.0 M), 510 mg 1-ethyl-4-[4-(4,4,5,5-tetramethyl-[1,3,2]dioxaborolan-2-yl)-benzenesulfonyl]-piperazine (compound C4), and 131 mg of trans-dichloro-bis(tricyclohexyl-phosphine)-palladium(II) at 110° C. for 18 hours. After aqueous work-up using 200 ml of dichloromethane and 75 ml of water, purification by chromatography on flash silica gel (eluent gradient dichloromethane/5-50 vol. % ethanol) yields 175 mg of the title compound as a waxy solid. ESI-MS: 511.3 (MH$^+$). TLC: Rf=0.30 (dichloromethane/ethanol 8:1 parts by volume).

B8. N-(2-Fluoro-4-methyl-phenyl)-4-{2-[2-(7-oxo-azepan-2-yl)-ethyl]-3H-imidazo[4,5-b]pyridin-6-yl}-benzenesulfonamide The title compound is synthesized as described for 7-(2-{6-[4-(azetidine-1-sulfonyl)-phenyl]-3H-imidazo[4,5-b]pyridin-2-yl}-ethyl)-azepan-2-one (compound B6) from 472 mg of 4-bromo-N-(2-fluoro-4-methyl-phenyl)-benzenesulfonamide (compound C5) and 300 mg of 7-[2-(6-bromo-3H-imidazo[4,5-b]pyridin-2-yl)-ethyl]-azepan-2-one (compound C1). Purification by chromatography on flash silica gel (eluent gradient: dichloromethane/5-20 vol. % ethanol) yields 185 mg of the title compound as a waxy solid. ESI-MS: 522.2 (MH$^+$). TLC: Rf=0.26 (dichloromethane/ethanol 10:1 parts by volume).

B9. 4-{2-[2-<7-Oxo-azepan-2-yl)-ethyl]-3H-imidazo[4,5-b]pyridin-6-yl}-N-o-tolyl-benzenesulfonamide The title compound is synthesized as described for 7-(2-{6-[4-(azetidine-1-sulfonyl)-phenyl]-3H-imidazo[4,5-b]pyridin-2-yl}-ethyl)-azepan-2-one (compound B6) from 372 mg of 4-bromo-N-o-tolyl-benzenesulfonamide (compound C6) and 250 mg of 7-[2-(6-bromo-3H-imidazo[4,5-b]pyridin-2-yl)-ethyl]-azepan-2-one (compound C1). Purification by chromatography on flash silica gel (eluent gradient: dichloromethane/0-25 vol. % ethanol) yields 138 mg of the title compound as a waxy solid. ESI-MS: 504.4 (MH$^+$). TLC: Rf=0.18 (dichloromethane/ethanol 10:1 parts by volume).

B10. N-Methyl-4-{2-[2-(7-oxo-azepan-2-yl)-ethyl]-3H-imidazo[4,5-b]pyridin-6-yl}-N-(tetrahydro-furan-2-ylmethyl)-benzenesulfonamide The title compound is synthesized as described for 7-(2-{6-[4-(azetidine-1-sulfonyl)-phenyl]-3H-imidazo[4,5-b]pyridin-2-yl}-ethyl)-azepan-2-one (compound B6) from 458 mg of 4-bromo-N-methyl-N-(tetrahydro-furan-2-ylmethyl)-benzenesulfonamide (compound C7) and 300 mg of 7-[2-(6-bromo-3H-imidazo[4,5-b]pyridin-2-yl)-ethyl]-azepan-2-one (compound C1). Purification by chromatography on flash silica gel (eluent gradient: dichloromethane/0-20 vol. % ethanol) yields 174 mg of the title compound as a waxy solid. ESI-MS: 512.4 (MH$^+$). TLC: Rf=0.30 (dichloromethane/ethanol 10:1 parts by volume).

C1. 7-[2-(6-Bromo-3H-imidazo[4,5-b]pyridin-2-yl)-ethyl]-azepan-2-one 665 mg of 7-[(E,Z)-2-(6-bromo-3H-imidazo[4,5-b]pyridin-2-yl)-vinyl]-3,4,5,6-tetrahydro-azepin-2-one (compound D1) are dissolved in 50 ml of methanol. Subsequently, 91 mg of Adam's catalyst (PtO2) is added and the suspension is vigorously stirred under an atmosphere of hydrogen at room temperature for 70 hours. Thereafter, the reaction mixture is evaporated to dryness, purified by flash chromatography (eluent gradient: dichloromethane/ethanol 0-10 vol. %), and lyophilized from 4.0 ml of water, 4.0 ml of dioxane, and 1.0 ml of ethanol to afford 236 mg of the title compound as an amorphous, colorless solid of m.p. 245° C. ESI-MS: 337.2/339.1 (MH$^+$, 100%:98%). TLC: Rf=0.47 (dichloromethane/ethanol 10:1 parts by volume).

C2. N,N-Dimethyl-4-(4,4,5,5-tetramethyl-[1,3,2]dioxaborolan-2-yl)-benzene-sulfonamide The compound is prepared according to WO 2004009086 A1.

C3. 1-(4-Bromo-benzenesulfonyl)-azetidine 4.09 g of azetidine are dissolved in a two-phase solvent system of 200 ml of dichloromethane and 130 ml of an aqueous potassium carbonate solution (strength 4.0 M). Subsequently, a solution of 15.25 g of commercially available 4-bromo-benzenesulfonyl chloride in 70 ml of dichloromethane is slowly added to the reaction mixture. Thereafter, the mixture is vigorously stirred for 17 hours at room temperature. For extraction, 200 ml of dichloromethane and 100 ml of water are added. The organic layer is dried using $Na_2SO_4$, filtered with suction, and concentrated in vacuo to yield 15.22 g of the title compound as a colorless, amorphous solid of m.p. 145° C. ESI-MS: 276.1/278.0 ($MH^+$, 100%:95%). TLC: Rf=0.59 (dichloromethane/ethanol 10:1 parts by volume).

C4. 1-Ethyl-4-[4-(4,4,5,5-tetramethyl-[1,3,2]dioxaborolan-2-yl)-benzenesulfonyl]-piperazine 2.29 g of 1-(4-bromo-benzenesulfonyl)-4-ethyl-piperazine (compound D3), 1.92 g of bis(pinacolato)diboron, 152 mg of $Pd(Cl)_2(dppf).CH_2Cl_2$, 114 mg of DPPF, and 2.02 g of potassium acetate are suspended in 30 ml of dioxane. Subsequently, the reaction mixture is heated at 100° C. for 5.5 hours during which time the former orange suspension becomes black. Thereafter, the reaction mixture is concentrated in vacuo. The remaining residue is extracted three times using 150 ml of dichloromethane each and 150 ml of water. The organic layer is dried ($Na_2SO_4$), filtered with suction and evaporated to dryness to yield 3.73 g of a crude material, which is purified by flash chromatography (eluent gradient: toluene/acetone 4:1 parts by volume+5-8 vol. % methanol) to afford 2.47 g of the title compound as an amorphous solid of m.p. 125° C. ESI-MS: 381.2 ($MH^+$). TLC: $R_f$=0.83 (dichloromethane/ethanol 8:1 parts by volume).

C5. 4-Bromo-N-(2-fluoro-4-methyl-phenyl)-benzenesulfonamide

The title compound is analogously synthesized as described for 1-(4-bromo-benzenesulfonyl)-azetidine (compound C3) from 767 mg of 4-bromo-benzenesulfonyl chloride, 451 mg of commercially available 2-fluoro-4-methyl-aniline in 12.0 ml of dichloromethane and 6.0 ml of $K_2CO_3$ solution to yield 727 mg of the title compound as colorless, amorphous solid of m.p. 111° C. ESI-MS: 361.2/363.3 ($MNH_4^+$, 100%:87%). TLC: Rf=0.57 (neat dichloromethane).

C6. 4-Bromo-N-o-tolyl-benzenesulfonamide

The title compound is analogously synthesized as described for 1-(4-bromo-benzenesulfonyl)-azetidine (compound C3) from 1.28 g of 4-bromo-benzenesulfonyl chloride, 643 mg of commercially available o-toluidine in 20 ml of dichloromethane and 10 ml of $K_2CO_3$ solution. Purification by chromatography on flash silica gel (eluent: neat dichloromethane) affords 830 mg of the title compound as colorless, amorphous solid of m.p. 114° C. GC-MS: 327.0 ($MH^+$). TLC: Rf=0.58 (neat dichloromethane).

C7. 4-Bromo-N-methyl-N-(tetrahydro-furan-2-ylmethyl)-benzenesulfonamide 4.30 g of 4-bromo-N-(tetrahydro-furan-2-ylmethyl)-benzenesulfonamide (compound D2) are dissolved in 150 ml of dry tetrahydrofuran. 590 mg of sodium hydride (strength 60 wt. % dispersion in mineral oil) are added in portions to the solution. After 15 min, 1.67 ml of methyl iodide are slowly added and the reaction mixture is stirred at room temperature for 20 hours. Subsequently, the suspension is concentrated in vacuo, extracted using 200 ml of ethyl acetate and 100 ml of half-saturated brine (sodium chloride solution). The organic layer is dried using $Na_2SO_4$, filtered with suction, and concentrated in vacuo to yield 4.53 g of the title compound as an oil. ESI-MS: 334.2/336.0 ($MH^+$, 100%:98%). TLC: Rf=0.78 (dichloromethane/ethanol 20:1 parts by volume).

D1. 7-[(E,Z)-2-(6-Bromo-3H-imidazo[4,5-b]pyridin-2-yl)-vinyl]-3,4,5,6-tetrahydro-azepin-2-one I) 503 mg of sodium hydride (strength 60 wt. % dispersion in mineral oil) are suspended in 90 ml of tetrahydrofuran under an atmosphere of dry nitrogen. Subsequently, a suspension of 4.23 g of (6-bromo-3H-imidazo[4,5-b]pyridin-2-ylmethyl)-tributyl-phosphonium chloride (compound I1) in 90 ml of tetrahydrofuran are added in the course of 5 min. Thereafter, the suspension is heated at 90° C. for 1 hour.

II) 1.70 g of 7-hydroxymethyl-azepan-2-on (compound F1) are dissolved in 180 ml of tetrahydrofuran under an atmosphere of dry nitrogen. Subsequently, 4.44 g of triacetoxy periodinane (Dess-Martin reagent) are added at room temperature and stirring is continued for further 3 hours. Thereafter, the suspension is carefully neutralized using sodium hydride (strength 60 wt. % dispersion in mineral oil) and added dropwise to the reaction mixture of I) at 90° C. during 20 min. Stirring at 90° C. is continued for 17 hours. Subsequently, the suspension is evaporated to dryness and purified by flash chromatography (eluent gradient dichloromethane/0-10 vol. % ethanol) to afford 809 mg of the title compound as an oil. ESI-MS: 333.2/335.2 ($MH^+$, 100%: 98%). TLC: Rf=0.44 (dichloromethane/ethanol 10:1 parts by volume).

Alternatively to the afore-described use of 7-oxo-azepane-2-carbaldehyde in-situ, isolated 7-oxo-azepane-2-carbaldehyde (compound E1) can be used in the Wittig reaction.

D2. 4-Bromo-N-(tetrahydro-furan-2-ylmethyl)-benzenesulfonamide 1.70 ml of commercially available tetrahydrofurfurylamine are dissolved in 45 ml of dry dichloromethane. A solution of 3.83 g of 4-bromo-benzenesulfonyl chloride in 20 ml of dichloromethane are slowly added at room temperature. Subsequently, 5.14 ml of Hünig's base are added and stirring is continued for 1.5 hours. For extraction, the reaction mixture is diluted with 150 ml of dichloromethane and 50 ml of water. The organic layer is dried using $Na_2SO_4$, filtered with suction, and concentrated in vacuo. Purification by chromatography on flash silica gel (eluent: dichloromethane/0-5 vol. % ethanol) affords 4.33 g of the title compound as an light yellow oil. ESI-MS: 320.3/322.1 ($MH^+$, 100%:98%). TLC: Rf=0.65 (dichloromethane/ethanol 20:1 parts by volume).

D3.
1-(4-Bromo-benzenesulfonyl)-4-ethyl-piperazine

The title compound is prepared according to WO 2003004472 A1.

E1. 7-Oxo-azepane-2-carbaldehyde 750 mg of 7-hydroxymethyl-azepan-2-on (compound F1) are dissolved in 85 ml of dichloromethane under an atmosphere of dry nitrogen. Subsequently, 2.22 g of triacetoxy periodinane (Dess-Martin reagent) are added at room temperature and stirring is continued for further 3 hours. Thereafter, the suspension is evaporated to dryness to yield 2.65 g of crude material. The crude product is purified by chromatography (eluent gradient: cyclohexane/50-100 vol. % ethyl acetate) to afford 272 mg of the title compound as a colorless, waxy solid. ESI-MS: 140.1 (MH$^+$). TLC: Rf=0.60 (dichloromethane/ethanol 10:1 parts by volume).

F1. 7-Hydroxymethyl-azepan-2-on 3.10 g of 7-oxo-azepane-2-carboxylic acid ethyl ester (compound G1) are dissolved in 150 ml of dichloromethane under an atmosphere of dry nitrogen. At room temperature, 8.45 ml of lithium boron hydride solution in tetrahydrofuran (strength 2.0 M) are slowly added to the solution in the course of 10 min. Thereafter, the reaction mixture is stirred for 17 hours overnight at room temperature. Subsequently, the mixture is cooled in an ice bath and acidified to pH 1 using hydrochloric acid (strength 3.0 M). Under stirring, the reaction mixture is allowed to warm up to room temperature. Thereafter, potassium carbonate is carefully added thereby re-adjusting neutral pH. The reaction mixture is filtered with suction and the filtrate is concentrated in vacuo. Purification is achieved by flash chromatography (eluent gradient: dichloromethane/0-10 vol. % ethanol) to yield 1.46 g of the title compound as colorless solid of m.p. 100° C. ESI-MS: 144.1 (MH$^+$). TLC: Rf=0.47 (dichloromethane/ethanol 10:1 parts by volume; iodine staining).

G1. 7-Oxo-azepane-2-carboxylic acid ethyl ester

The title compound is synthesized according to a procedure described by L. Benati et al., *J. Org. Chem.* 1999, 64(21), 7836-7841 using compound H1.

H1. 1-Azido-2-oxo-cyclohexanecarboxylic acid ethyl ester

The title compound is synthesized according to procedures described by L. Benati et al., *J. Org. Chem.* 1999, 64(21), 7836-7841 and L. Benati et al., *J. Org. Chem.* 1999, 64(14), 5132-5138.

I1. (6-Bromo-3H-imidazo[4,5-b]pyridin-2-ylmethyl)-tributyl-phosphonium chloride 4.0 g of 6-bromo-2-chloromethyl-3H-imidazo[4,5-b]pyridine (compound J1) are suspended in 16 ml of N,N-dimethylformamide and 54 ml of acetonitrile. 4.9 ml of triphenylphosphine and 0.599 g of tetrabutylammonium iodide are added sequentially at 40° C. and the mixture is heated to 90° C. for 20 h. The mixture is concentrated to dryness to give the 8.94 g of the crude title compound as an oil, which is used as obtained. MS: 412.3, 414.2 (M$^+$). TLC: Rf=0.40-0.55 (dichloromethane/methanol 10:1 parts by volume).

Alternatively, 4.0 g of 6-bromo-2-chloromethyl-3H-imidazo[4,5-b]pyridine (compound J1) are suspended in 17 ml of N,N-dimethylformamide and 54 ml of acetonitrile. 4.8 ml of tributylphosphine and 600 mg of tetrabutylammonium iodide are added sequentially at 40° C. Subsequently, the mixture is heated to 90° C. for 18 hours. The mixture is concentrated to dryness to give 8.94 g of the crude title compound as an oil, which is purified by chromatography on flash silica gel (eluent gradient: dichloromethane/5-20 vol. % 2-propanol). The remaining residue is re-dissolved in 150 ml of ethyl acetate. Upon standing at room temperature, a precipitate of the title compound is formed, which is collected by filtration and dried under high vacuum to yield 4.52 g of (6-bromo-3H-imidazo[4,5-b]pyridin-2-ylmethyl)-tributyl-phosphonium chloride as an amorphous solid of m.p. 180° C. ESI-MS: 412.5, 414.4 (M$^+$, 100%:98%). TLC: Rf=0.45-0.55 (dichloromethane/methanol 10:1 parts by volume).

J1.
6-Bromo-2-chloromethyl-3H-imidazo[4,5-b]pyridine 3.0 g of 5-bromo-2,3-diaminopyridine (S.-X. Cai et al., *J. Med. Chem.* 1997, 40(22), 3679-3686) in 120 g of polyphosphoric acid are heated at 160° C. for 0.5 h. The solution is cooled to 100° C. and 1.26 ml of chloroacetonitrile are added. Thereafter, the reaction mixture is heated to 170° C. for 22 h. After cooling, the polyphosphoric acid is hydrolysed with 81 ml of water. After reheating to 90° C., charcoal is added under vigorous stirring. Subsequently, the suspension is filtered through a celite pad while still hot (70° C.). The filter cake is rinsed with 85 ml of water. The filtrate is adjusted to pH 4 using 9.0 M aqueous sodium hydroxide solution. The precipitate is collected, suspended in 100 ml of hot methanol and filtered over celite. The filtrate is concentrated to dryness to afford 2.78 g of the title compound as a beige, amorphous solid of m.p. >325° C. MS: 246.2/248.2/250.3 (MH$^+$, 77%/100%/25%). TLC: R$_f$=0.42 (dichloromethane/methanol 10:1 parts by volume).

Commercial Applicability

The compounds according to the invention have valuable pharmacological properties which make them commercially utilizable. They are selective inhibitors of the enzyme inducible nitric oxide synthase. Nitric oxide synthases (NO-syntases, NOSs) are enzymes that generate NO and citrulline from the amino acid arginine. In certain pathophysiological situations such as arginine depletion or tetrahydrobiopterin depletion the generation of O$_2^-$ from NO-synthases instead or together with NO has been reported. NO is long known as a signalling molecule in most living organisms including mammals and humans. The most prominent action of NO is it's smooth muscle relaxing activity, which is caused on the molecular level by the activation of soluble guanylate cyclase. In the last years a lot of other enzymes have been shown to be regulated by NO or reaction products of NO. There exist three isoforms of NO-synthases which fall into two classes and differ in their physiologic functions and molecular properties. The first class, known as constitutive NO-synthases, comprises of the endothelial NO-synthase and the neuronal NO-synthase. Both isoenzymes are expressed constitutively in various cell types, but are most prominent in endothelial cells of blood vessel walls (therefore called endothelial NO-synthase, eNOS or NOS-III) and in neuronal cells (therefore called neuronal NO-synthase, nNOS or NOS-I). Activation of these two enzymes is dependent on Ca$^{2+}$/Calmodulin which is generated by transient increases of the intracellular free Ca²⁺ concentration. Activation of constitutive isoforms leads to transient bursts of nitric oxide resulting in nanomolar cellular or tissue NO concentrations. The endothelial isoform is involved in the physiologic regulation of blood pressure. NO generated by the neuronal isoform seems to have neurotransmitter function and the neuronal isoform is among other regulatory processes involved in memory function (long term potentiation).

In contrast to the constitutive isoforms the activation of inducible NO-synthase (iNOS, NOS-II), the sole member of the second class, is performed by transcriptional activation of the iNOS-promoter. Proinflammatory stimuli lead to transcription of the gene for inducible NO-synthase, which is catalytically active without increases in the intracellular $Ca^{2+}$-concentration. Due to the long half life of the inducible NO-synthase and the unregulated activity of the enzyme, high micromolar concentrations of NO are generated over longer time periods. These high NO-concentrations alone or in cooperation with other reactive radicals such as $O_2^-$ are cytotoxic. Therefore, in situations of microbial infections, iNOS is involved in cell killing by macrophages and other immune cells during early nonspecific immune responses.

There are a number of pathophysiological situations which among others are characterized by the high expression of inducible NO-synthase and concomitant high NO or $O_2^-$ concentrations. It has been shown that these high NO concentrations alone or in combination with other radical species lead to tissue and organ damage and are causally involved in these pathophysiologies. As inflammation is characterized by the expression of proinflammatory enzymes, including inducible NO-synthase, acute and chronic inflammatory processes are promising diseases for the therapeutic application of selective inhibitors of inducible NO-synthase. Other pathophysiologies with high NO-production from inducible NO-synthase are several forms of shock (septic, hemorrhagic and cytokine-induced). It is clear that nonselective NO-synthase inhibitors will lead to cardiovascular and neuronal side effects due to concomitant inhibition of constitutive NO-synthase isoforms.

It has been shown in in-vivo animal models of septic shock that reduction of circulating plasma NO-levels by NO-scavenger or inhibition of inducible NO-synthase restores systemic blood pressure, reduces organ damage and increases survival (deAngelo Exp. Opin. Pharmacother. 19-29, 1999; Redl et al. Shock 8, Suppl. 51, 1997; Strand et al. CnlCare Med. 26, 1490-1499, 1998). It has also been shown that increased NO production during septic shock contributes to cardiac depression and myocardial dysfunction (Sun et al. J. Mol. Cell Cardiol. 30, 989-997, 1998). Furthermore there are also reports showing reduced infarct size after occlusion of the left anterior coronary artery in the presence of NO-synthase inhibitors (Wang et al. Am. J. Hyperttens. 12, 174-182, 1999). Considerable inducible NO-synthase activity is found in human cardiomyopathy and myocarditis, supporting the hypothesis that NO accounts at least in part for the dilatation and impaired contractility in these pathophysiologies (de Belder et al. Br. Heart. J. 4, 426-430, 1995).

In animal models of acute or chronic inflammation, blockade of inducible NO-synthase by isoform-selective or nonselective inhibitors or genetic knock out improves therapeutic outcome. It is reported that experimental arthritis (Connor et al. Eur. J. Pharmacol. 273, 15-24, 1995) and osteoarthritis (Pelletier et al. Arthritis & Rheum. 41, 1275-1286, 1998), experimental inflammations of the gastro-intestinal tract (Zingarelli et al. Gut 45, 199-209, 1999), experimental glomerulonephritis (Narita et al. Lab. Invest. 72, 17-24, 1995), experimental diabetes (Corbett et al. PNAS 90, 8992-8995, 1993), LPS-induced experimental lung injury is reduced by inhibition of inducible NO-synthase or in iNOS-knock out mice (Kristof et al. Am. J. Crit. Care. Med. 158, 1883-1889, 1998). A pathophysiological role of inducible NO-synthase derived NO or $O_2^-$ is also discussed in chronic inflammatory diseases such as asthma, bronchitis and COPD (chronic obstructive pulmonary disease).

Furthermore, in models of neurodegenerative diseases of the central nervous system (CNS) such as MPTP-induced parkinsonism (MPTP=1-methyl-4-phenyl-1,2,3,6-tetrahydropyridine), amyloid peptide induced Alzheimer's disease (Ishii et al., FASEB J. 14, 1485-1489, 2000), malonate induced Huntington's disease (Connop et al. Neuropharmacol. 35, 459-465, 1996), experimental meningitis (Korytko & Boje Neuropharmacol. 35, 231-237, 1996) and experimental encephalitis (Parkinson et al. J. Mol. Med. 75, 174-186, 1997) a causal participation of NO and inducible NO-synthase has been shown.

Increased iNOS expression has been found in the brains of AIDS (acquired immunodeficiency syndrome) victims and it is reasonable to assume a role of iNOS in AIDS related dementia (Bagasra et al. J. Neurovirol. 3 153-167, 1997).

Other studies implicated nitric oxide as a potential mediator of microglia dependent primary demyelination, a hallmark of multiple sclerosis (Parkinson et al. J. Mol. Med. 75, 174-186, 1997).

An inflammatory reaction with concomitant expression of inducible NO-synthase also takes place during cerebral ischemia and reperfusion (Iadecola et al. Stroke 27, 1373-1380, 1996). Resulting NO together with $O_2^-$ from infiltrating neutrophils is thought to be responsible for cellular and organ damage.

Also, in models of traumatic brain injury (Mesenge et al. J. Neurotrauma 13, 209-214, 1996; Wada et al. Neurosurgery 43, 1427-1436, 1998) NO-synthase inhibitors have been shown to possess protective properties. A regulatory role for inducible NO-synthase has been reported in various tumor cell lines (Tozer & Everett Clin Oncol. 9. 357-264. 1997).

On account of their inducible NO-synthase-inhibiting properties, the compounds according to the invention can be employed in human and veterinary medicine and therapeutics, where an excess of NO or $O_2^-$ due to increases in the activity of inducible NO-synthase is involved. They can be used without limitation for the treatment and prophylaxis of the following diseases:

Acute inflammatory diseases: Septic shock, sepsis, SIRS (systemic inflammatory response syndrome), hemorrhagic shock, shock states induced by cytokine therapy [IL-2 (interleukin-2), TNF (tumor necrosis factor)], septic and postoperative ileus, organ transplantation and transplant rejection, head trauma, acute lung injury, ARDS (acute respiratory distress syndrome), inflammatory skin conditions such as sunburn, inflammatory eye conditions such as uveitis, glaucoma and conjunctivitis.

Chronic inflammatory diseases of peripheral organs and the CNS: gastrointestinal inflammatory diseases such as Crohn's disease, inflammatory bowel disease, ulcerative colitis, lung inflammatory diseases such as asthma and COPD as well as allergic rhinitis, arthritic disorders such as rheumatoid arthritis, osteoarthritis and gouty arthritis, heart disorders such as cardiomyopathy and myocarditis, atherosclerosis, neurogenic inflammation, skin diseases such as psoriasis, dermatitis and eczema, diabetes, glomerulonephritis; dementias such as dementias of the Alzheimer's type, vascular dementia, dementia due to a general medical condition, such as AIDS, Parkinson's disease, Huntington's induced dementias, ALS (amyotrophic lateral sclerosis), multiple sclerosis;

necrotizing vasculitides such as polyarteritis nodosa, serum sickness, Wegener's granulomatosis, Kawasaki's syndrome; headaches such as migraine, chronic tension headaches, cluster and vascular headaches, post-traumatic stress disorders; pain disorders such as neuropathic pain; myocardial and cerebral ischemia/reperfusion injury.

The compounds may also be useful in the treatment of cancers that express nitric oxide synthase.

In the context of their properties, functions and usabilities mentioned herein, the compounds according to the invention are distinguished by valuable and desirable effects related therewith, such as, for example, high efficacy, high selectivity, low toxicity, superior bioavailability in general (e.g. good enteral absorption, low microsomal clearance, low serum protein binding), superior therapeutic window, absence of significant side effects and further beneficial effects related with their therapeutic and pharmaceutical suitability.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions having an iNOS inhibitory activity.

The invention furthermore relates to pharmaceutical compositions for the treatment and/or prophylaxis of the illnesses mentioned, which contain one or more of the compounds according to the invention.

The invention moreover relates to pharmaceutical compositions according to this invention having an iNOS inhibitory activity.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches [e.g. as TTS (transdermal therapeutic systems)], emulsions, suspensions, gels or solutions, the active compound content advantageously being between 0.1 and 95 wt. % and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 μm, advantageously of 2 to 6 μm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for iNOS inhibitors. Topical application forms (such as ointments) for the treatment of dermatoses thus contain the active compounds in a concentration of, for example, 0.1-99 wt. %. The dose for administration by inhalation is customarily between 0.1 and 10 mg per day. The customary dose in the case of systemic therapy (p.o.) is between 0.3 and 30 mg/kg per day, (i. v.) is between 0.3 and 30 mg/kg/h.

Biological Investigations

Measurement of Inducible NO-Synthase Activity

The assay is performed in 96-well microtiter F-plates (Greiner, Frickenhausen, FRG) in a total volume of 100 μl in the presence of 100 nM calmodulin, 226 μM $CaCl_2$, 477 μM $MgCl_2$, 5 μM flavin-adenine-dinucleotide (FAD), 5 μM flavin mononucleotide (FMN), 0.1 mM nicotinamide adenine dinucleotide phosphate (NADPH), 7 mM glutathione, 10 μM tetrahydrobiopterine (BH4) and 100 mM 4-(2-hydroxyethyl)

piperazine-1-ethanesulfonic acid (HEPES) pH 7.2. Arginine concentrations are 0.1 µM for enzyme inhibition experiments. 150000 dpm of [³H]arginine are added to the assay mixture. Enzyme reaction is started by the addition of 4 µg of a crude cytosolic fraction containing human inducible NO-synthase and the reaction mixture is incubated for 45 to 60 min at 37° C. Enzyme reaction is stopped by adding 10 µl of 2M 2-morpholinoethane sulfonic acid buffer (MES-buffer) pH 5.0. 50 µl of the incubation mixture are transferred into a MADP N65 filtration microtiter plate (Millipore, Eschborn, FRG) containing already 50 µl of AG-50W-X8 cation exchange resin (Biorad, München, FRG). The resin in the Na loaded form is pre-equilibrated in water and 70 µl (corresponding to 50 µl dry beads) are pipetted under heavy stirring with a 8 channel pipette into the filtration plate. After pipetting 50 µl of the enzyme reaction mixture onto the filtration plates, the plates are placed on a filtration manifold (Porvair, Shepperton, UK) and the flow through is collected in Pico scintillation plates (Packard, Meriden, Conn.). The resin in the filtration plates is washed with 75 µl of water (1×50 µl and 1×25 µl) which is also collected in the same plate as the sample. The total flow through of 125 µl is mixed with 175 µl of Microscint-40 scintillation cocktail (Packard) and the scintillation plate is sealed with TopSeal P-foil (Packard). Scintillation plates are counted in a szintillation counter.

For the measurement of inducible NO-synthase-inhibiting potencies of compounds according to the invention increasing concentrations of inhibitors are included into the incubation mixture. IC$_{50}$ values are calculated from the percent inhibition at given concentrations by nonlinear least square fitting.

Representative inhibitory values which are determined for compounds according to the invention follow from the following table A, in which the compound numbers correspond to the example numbers.

Measurement of Inducible NO-Synthase Activity in the Presence of 20% Human Plasma Serum The assay determining the human plasma serum binding of compounds according to the invention was performed essentially as the enzymatic activity assay described above. Human plasma serum 20% (v/v) was added into the reaction volume. Human serum was obtained after coagulation and sedimentation of drawn donor blood. After centrifugation (two times 3500 rpm, 30 min) the plasma serum was dialyzed in phosphate buffered saline (PBS) for 18 h using dialysis cassettes with a molecular weight cuttoff of 3500 Dalton (Slide-a-Lyzer 3.5 K, Pierce, Rockford Ill.) in order to reduce the L-arginine concentration that is interfering with the radioactive activity assay. The buffer was refreshed 5 times during dialysis. The serum was aliquoted and frozen at −20° C. until use. Inhibitory potency of the compounds according to the invention was determined as described above.

Representative values for compounds according to the invention are given in the following table A, in which the compound numbers correspond to the example numbers.

TABLE A

| Inhibition of iNOS activity [measured as -logIC$_{50}$ (mol/l)] | | |
|---|---|---|
| compound | -logIC$_{50}$ | -logIC$_{50}$ 20% human serum |
| 1 | 6.77 | 6.00 |
| 2 | 6.65 | 6.40 |
| 3 | 6.60 | 5.80 |
| 4 | 6.64 | 6.02 |

TABLE A-continued

| Inhibition of iNOS activity [measured as -logIC$_{50}$ (mol/l)] | | |
|---|---|---|
| compound | -logIC$_{50}$ | -logIC$_{50}$ 20% human serum |
| 5 | 6.64 | 6.03 |
| 6 | 6.52 | 6.22 |
| 7 | 6.33 | |
| 8 | 6.23 | |
| 9 | 6.40 | |
| 10 | 6.21 | |

The invention claimed is:

1. A compound of formula I

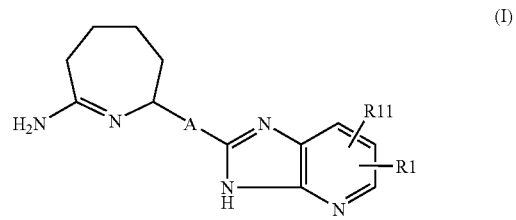

(I)

in which

A is 1-4C-alkylene or 3-7C-cycloalkylene,

R1 is phenyl, R2- and/or R3-substituted phenyl, Har1, or R4-and/or R5-substituted Har1, R11 is hydrogen, halogen, 1-4C-alkyl or 1-4C-alkoxy, in which R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, Phenyl-1-4C-alkoxy, or —SO$_2$—N(R21)R22, in which R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which Har2 is pyridyl, thienyl, furyl or tetrahydrofuryl, R211 is 1-4C-alkyl, halogen, 1-4C-alkoxy, or mono- or di-1-4C-alkylamino, R212 is 1-4C-alkyl or halogen, R22 is hydrogen, 1-4C-alkyl, hydroxy-2-4C-alkyl or 1-4C-alkoxy-2-4C-alkyl, or R21 and R22 together and with inclusion of the nitrogen atom, to which they are bonded, form a heterocyclic ring Het1, in which Het1 is a fully saturated or partially unsaturated mono- or fused bicyclic ring or ring system made up of a first constituent being a 3- to 7-membered monocyclic fully saturated non-aromatic heterocyclic ring B, which heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzene ring, and which ring Het1 is optionally substituted by R23 on a ring carbon atom, and/or which ring Het1 is optionally substituted by R24 on a further ring carbon atom,
and/or which ring Het1 is optionally substituted by an ethylenedioxy group on a ring carbon atom,
and/or which ring Het1 is optionally substituted by R25 on a ring nitrogen atom,
in which
R23 is 1-4C-alkyl, 1-4C-alkoxy or phenylcarbonyl,
R24 is 1-4C-alkyl or 1-4C-alkoxy,
R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which
R251 is halogen, cyano or 1-4C-alkyl,
R252 is halogen or 1-4C-alkyl,
R3 is hydrogen, 1-4C-alkyl, halogen, trifluoromethyl, 1-4C-alkoxy, or completely or predominantly fluorine-substituted 1-4C-alkoxy,
Har1 is bonded to the parent molecular group via a ring carbon atom, and is a monocyclic or fused bicyclic 5- to 10-membered unsaturated or partially saturated heteroaryl radical comprising one to three heteroatoms, each of which is selected from the group consisting of nitrogen, oxygen and sulfur,
R4 is 1-4C-alkyl, halogen, cyano, trifluoromethyl, phenyl, mono- or di-1-4C-alkylamino, formyl, 1-4C-alkylcarbonyl, carboxyl or 1-4C-alkoxy,
R5 is 1-4C-alkyl or halogen,
or an enantiomer, salt, or salt of an enantiomer thereof.

2. A compound according to claim 1
in which
A is 1-4C-alkylene or 3-7C-cycloalkylene,
R1 is phenyl, R2- and/or R3-substituted phenyl, Har1, or R4- and/or R5-substituted Har1,
R11 is hydrogen, halogen, 1-4C-alkyl or 1-4C-alkoxy,
in which
R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22,
in which
R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which
Har2 is pyridyl, thienyl or furyl,
R211 is 1-4C-alkyl, halogen, 1-4C-alkoxy, or mono- or di-1-4C-alkylamino,
R212 is 1-4C-alkyl or halogen,
R22 is hydrogen, 1-4C-alkyl, hydroxy-2-4C-alkyl or 1-4C-alkoxy-2-4C-alkyl,
or R21 and R22 together and with inclusion of the nitrogen atom, to which they are bonded, form a heterocyclic ring Het1, in which
Het1 is a fully saturated or partially unsaturated mono- or fused bicyclic ring or ring system made up of
a first constituent being a 3- to 7-membered monocyclic fully saturated non-aromatic heterocyclic ring B, which heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent,
a second constituent being a benzene ring,
and which ring Het1 is optionally substituted by R23 on a ring carbon atom,
and/or which ring Het1 is optionally substituted by R24 on a further ring carbon atom,
and/or which ring Het1 is optionally substituted by an ethylenedioxy group on a ring carbon atom,
and/or which ring Het1 is optionally substituted by R25 on a ring nitrogen atom,
in which
R23 is 1-4C-alkyl, 1-4C-alkoxy or phenylcarbonyl,
R24 is 1-4C-alkyl or 1-4C-alkoxy,
R25 is 1-4C-alkyl, phenyl-1-4C-alkyl, 1-4C-alkylcarbonyl, 1-4C-alkoxy-2-4C-alkyl,
mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which
R251 is halogen, cyano or 1-4C-alkyl,
R252 is halogen or 1-4C-alkyl,
R3 is hydrogen, 1-4C-alkyl, halogen, trifluoromethyl, 1-4C-alkoxy, or completely or predominantly fluorine-substituted 1-4C-alkoxy,
Har1 is bonded to the parent molecular group via a ring carbon atom, and is a monocyclic or fused bicyclic 5- to 10-membered unsaturated or partially saturated heteroaryl radical comprising one to three heteroatoms, each of which is selected from the group consisting of nitrogen, oxygen and sulfur,
R4 is 1-4C-alkyl, halogen, cyano, trifluoromethyl, phenyl, mono- or di-1-4C-alkylamino, formyl, 1-4C-alkylcarbonyl, carboxyl or 1-4C-alkoxy,
R5 is 1-4C-alkyl or halogen,
or an enantiomer, salt, or salt of an enantiomer thereof.

3. A compound according to claim 1
in which
A is ethylene or cyclopropylene,
R1 is bonded to the 6-position of the imidazopyridine scaffold, and is phenyl, R2- and/or R3-substituted phenyl, or Hart1,
R11 is hydrogen,
in which
R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, phenyl-1-4C-alkoxy, or —SO$_2$—N(R21)R22,
in which
R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which
Har2 is pyridyl, thienyl or furyl,
R211 is 1-4C-alkyl, halogen, 1-4C-alkoxy, or mono- or di-1-4C-alkylamino,
R212 is 1-4C-alkyl or halogen,
R22 is hydrogen, hydroxy-2-4C-alkyl, 1-4C-alkoxy-2-4C-alkyl or 1-4C-alkyl,
or R21 and R22 together and with inclusion of the nitrogen atom, to which they are bonded, form a heterocyclic ring Het1, in which
Het1 is piperidinyl, pyrrolidinyl, azetidinyl, morpholinyl, thiomorpholinyl, S-oxo-thiomorpholinyl or S,S-dioxothiomorpholinyl, indolinyl, isoindolinyl, 1,2,3,4-tetrahydroquinolinyl, 1,2,3,4-tetrahydroisoquinolinyl, piperazinyl, homopiperazinyl, 4N-(R25)-piperazinyl, 4N-(R25)-homopiperazinyl, 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl, 5-oxo-1,4-diazepanyl, 3-(R25)-imidazolidin-2-one-yl, 3-(R25)-imidazolidin-2,5-dione-yl, 4-(R25)-piperazine-2-one-yl, 4-(R25)-piperazine-2,6-dione-yl or 4-(R25)-1,4-diazepan-5-one-yl, in which R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, Har1 is bonded to the parent molecular group via a ring carbon atom, and is pyridyl, thienyl, furanyl, indolyl, benzothienyl, benzofuranyl, benzoxazolyl, benzothiazolyl, quinolyl or isoquinolyl, or an enantiomer, salt, or salt of an enantiomer thereof.

4. A compound according to claim 1
in which
A is ethylene,
R1 is bonded to the 6-position of the imidazopyridine scaffold, and is phenyl, or R2- and/or R3-substituted phenyl,
R11 is hydrogen,
in which
R2 is cyano, halogen, carboxyl, 1-4C-alkyl, 1-4C-alkoxy, aminocarbonyl, mono- or di-1-4C-alkylaminocarbonyl, 1-4C-alkylcarbonylamino, 1-4C-alkoxycarbonyl, amino, mono- or di-1-4C-alkylamino, trifluoromethyl, hydroxyl, 1-4C-alkylsulfonylamino, phenylsulfonylamino, or phenyl-1-4C-alkoxy,
R3 is hydrogen, 1-4C-alkyl, halogen, trifluoromethyl, 1-4C-alkoxy, or completely or predominantly fluorine-substituted 1-4C-alkoxy,
or an enantiomer, salt, or salt of an enantiomer thereof.

5. A compound according to claim 1
in which
A is ethylene,
R1 is bonded to the 6-position of the imidazopyridine scaffold, and is R2- and/or R3-substituted phenyl or Har1,
R11 is hydrogen,
in which
R2 is —SO$_2$—N(R21)R22, in which
R21 is hydrogen, 1-4C-alkyl, 3-7C-cycloalkyl, phenyl-1-4C-alkyl, Har2-1-4C-alkyl, hydroxy-2-4C-alkyl, 1-4C-alkoxy-2-4C-alkyl, phenyl, pyridyl, or R211- and/or R212-substituted phenyl, in which
Har2 is pyridyl, thienyl or furyl,
R211 is 1-4C-alkyl, halogen, 1-4C-alkoxy, or mono- or di-1-4C-alkylamino,
R212 is 1-4C-alkyl or halogen,
R22 is hydrogen, hydroxy-2-4C-alkyl, 1-4C-alkoxy-2-4C-alkyl or 1-4C-alkyl,
or R21 and R22 together and with inclusion of the nitrogen atom, to which they are bonded, form a heterocyclic ring Het1, in which
Het1 is piperidinyl, pyrrolidinyl, azetidinyl, morpholinyl, thiomorpholinyl, S-oxo-thiomorpholinyl or S,S-dioxo-thiomorpholinyl, indolinyl, isoindolinyl, 1,2,3,4-tetrahydroquinolinyl, 1,2,3,4-tetrahydroisoquinolinyl, piperazinyl, homopiperazinyl, 4N-(R25)-piperazinyl, 4N-(R25)-homopiperazinyl, 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, 2,6-dioxopiperazinyl, 5-oxo-1,4-diazepanyl, 3-(R25)-imidazolidin-2-one-yl, 3-(R25)-imidazolidin-2,5-dione-yl, 4-(R25)-piperazine-2-one-yl, 4-(R25)-piperazine-2,6-dione-yl or 4-(R25)-1,4-diazepan-5-one-yl, in which R25 is 1-4C-alkyl, phenyl-1-4C-alkyl, 1-4C-alkylcarbonyl, 1-4C-alkoxy-2-4C-alkyl, mono- or di-1-4C-alkylamino-2-4C-alkyl, phenyl, pyrimidyl, pyridyl, formyl, 3-7C-cycloalkyl, 3-7C-cycloalkylmethyl, or R251- and/or R252-substituted phenyl, in which R251 is halogen, cyano or 1-4C-alkyl, R252 is halogen or 1-4C-alkyl, R3 is hydrogen, 1-4C-alkyl, halogen, trifluoromethyl, 1-4C-alkoxy, or completely or predominantly fluorine-substituted 1-4C-alkoxy, Har1 is bonded to the parent molecular group via a ring carbon atom, and is pyridyl, thienyl, furanyl, indolyl, benzothienyl, benzofuranyl, benzoxazolyl, benzothiazolyl, quinolyl or isoquinolyl, or an enantiomer, salt, or salt of an enantiomer thereof.

6. A compound according to claim 1
in which
A is 1-4C-alkylene,
Ri is phenyl, R2-substituted phenyl or Har1,
R11 is hydrogen,
in which
R2 is cyano, 1-4C-alkoxy or —SO$_2$—N(R21)R22, in which
R21 is hydrogen, 1-4C-alkyl, Har2-1-4C-alkyl, phenyl or R211- and/or R212-substituted phenyl, in which
Har2 is furyl or tetrahydrofuranyl,
R211 is 1-4C-alkyl or halogen,
R212 is 1-4C-alkyl or halogen,
R22 is hydrogen or 1-4C-alkyl,
or R21 and R22 together and with inclusion of the nitrogen atom, to which they are bonded, form a heterocyclic ring Het1, in which
Het1 is a 3- to 7-membered monocyclic fully saturated non-aromatic heterocyclic ring B, which heterocyclic ring B comprises one to three heteroatoms independently selected from the group consisting of nitrogen, oxygen and sulfur,
and which ring Het1 is optionally substituted by R23 on a ring carbon atom,
and/or which ring Het1 is optionally substituted by R25 on a ring nitrogen atom,
in which
R23 is 1-4C-alkyl,
R25 is 1-4C-alkyl,
Har1 is bonded to the parent molecular group via a ring carbon atom, and is a monocyclic or fused bicyclic 5- to 10-membered unsaturated heteroaryl radical comprising one to three heteroatoms, each of which is selected from the group consisting of nitrogen, oxygen and sulfur,
or an enantiomer, salt, or salt of an enantiomer thereof.

7. A compound according to claim 1
in which
A is ethylene,
R1 is phenyl, R2-substituted phenyl or Har1
R11 is hydrogen,
in which R2 is cyano, 1-4C-alkoxy or —SO₂—N(R21)R22, in which R21 is hydrogen, 1-4C-alkyl, Har2-1-4C-alkyl or R211- and/or R212-substituted phenyl, in which Har2 is tetrahydrofuranyl, R211 is 1-4C-alkyl or halogen, R212 is 1-4C-alkyl, R22 is hydrogen or 1-4C-alkyl, or R21 and R22 together and with inclusion of the nitrogen atom, to which they are bonded, form a heterocyclic ring Het1, in which Het1 is a 4- to 6-membered monocyclic fully saturated non-aromatic heterocyclic ring B, which heterocyclic ring B comprises one to three nitrogen atoms, and which ring Het1 is optionally substituted by R25 on a ring nitrogen atom, in which R25 is 1-4C-alkyl, Har1 is bonded to the parent molecular group via a ring carbon atom, and is a fused bicyclic 9-membered unsaturated heteroaryl radical comprising one oxygen atom, or an enantiomer, salt, or salt of an enantiomer thereof.

8. A compound according to claim 1
in which
A is ethylene,
Ri is phenyl, R2-substituted phenyl or Har1,
R11 is hydrogen,
in which
R2 is cyano, 1-4C-alkoxy or —SO₂—N(R21)R22, in which
R21 is hydrogen, 1-4C-alkyl, Har2-1-4C-alkyl or R211- and/or R212-substituted phenyl, in which
Har2 is tetrahydrofuranyl,
R211 is 1-4C-alkyl or halogen,
R212 is 1-4C-alkyl,
R22 is hydrogen or 1-4C-alkyl, or R21 and R22 together and with inclusion of the nitrogen atom, to which they are bonded, form a heterocyclic ring Het1, in which Het1 is an azetidinyl or piperazinyl ring, which ring Het1 is optionally substituted by R25 on a ring nitrogen atom, in which R25 is 1-4C-alkyl, Har1 is bonded to the parent molecular group via a ring carbon atom, and is a benzofuranyl ring, or an enantiomer, salt, or salt of an enantiomer thereof.

9. A compound according to claim 8 selected from the group consisting of 7-[2-(6-phenyl-3H-imidazo[4,5-b]pyridin-2-yl)-ethyl]-4,5,6,7-tetrahydro-3H-azepin-2-ylamine, 7-[2-(6-{4-cyano-phen-1-yl}-3H-imidazo[4,5-b]pyridin-2-yl)-ethyl]-4,5,6,7-tetrahydro-3H-azepin-2-ylamine, 7-{2-[6-(4-methoxy-phenyl)-3H-imidazo[4,5-b]pyridin-2-yl]-ethyl}-4,5,6,7-tetrahydro-3H-azepin-2-ylamine, 7-[2-(6-benzofuran-2-yl-3H-imidazo[4,5b]pyridin-2-yl)-ethyl]-4,5,6,7-tetrahydro-3H-azepin-2-ylamine, 4-{2-[2-(7-amino-3,4,5,6-tetrahydro-2H-azepin-2-yl)-ethyl  ]-3H-imidazo[4,5b]pyridin-6-yl}-N,N-dimethyl-benzenesulfonamide, 7-(2-{6-[4-(azetidine-1-sulfonyl)-phenyl]-3H-imidazo[4,5-b]pyridin-2-yl}-ethyl)-4,5,6,7-tetrahydro-3H-azepin-2-ylamine, 7-(2-{6[4-(4-ethyl-piperazine-1-sulfonyl)-phenyl]-3H-imidazo[4,5-b]pyridin-2-yl}-ethyl)-4,5,6,7-tetrahydro-3H-azepin-2-ylamine, 4-{2-[2-(7-amino-3,4,5,6-tetrahydro-2H-azepin-2-yl)-ethyl]-3H-imidazo [4,5-b]pyridin-6-yl}-N-(2-fluoro-4-methyl-phenyt)-benzenesulfonamide, 4-{2-[2-(7-armino-3,4,5,6-tetrahydro-2H-azepin-2-yl)-ethyl]-3H-imidazo[4,5-b]pyridin-6-yl}-N-o-tolyl-benzenesulfonamide and 4-{2[2-(7-amino-3,4,5,6-tetrahydro-2H-azepin-2-yl)-ethyl]-3H-imidazo [4,5-b]pyridin-6-yl}-N-methyl-N-(tetrahydro-furan-2-ylmethyl)-benzenesulfonamide.

10. A pharmaceutical composition containing one or more compounds according to claim 1 together with a pharmaceutically acceptable auxiliary and/or excipient.

* * * * *